(12) United States Patent
Britton et al.

(10) Patent No.: US 11,654,103 B2
(45) Date of Patent: *May 23, 2023

(54) SKIN CARE FORMULATION

(71) Applicant: EMBRYOGENESIS PTY LTD, South Hurstville (AU)

(72) Inventors: Peter Britton, Carlton (AU); Andrew French, Carlton (AU)

(73) Assignee: EMBRYOGENESIS PTY LTD

( * ) Notice: Subject to any disclaimer, the term of this patent is extended or adjusted under 35 U.S.C. 154(b) by 981 days.

This patent is subject to a terminal disclaimer.

(21) Appl. No.: 16/322,703

(22) PCT Filed: Aug. 1, 2017

(86) PCT No.: PCT/AU2017/000158
§ 371 (c)(1),
(2) Date: Feb. 1, 2019

(87) PCT Pub. No.: WO2018/023148
PCT Pub. Date: Feb. 8, 2018

(65) Prior Publication Data
US 2021/0330579 A1 Oct. 28, 2021

Related U.S. Application Data

(60) Provisional application No. 62/369,240, filed on Aug. 1, 2016.

(51) Int. Cl.
| | |
|---|---|
| *A61K 8/14* | (2006.01) |
| *A61K 8/64* | (2006.01) |
| *A61K 8/98* | (2006.01) |
| *A61K 8/9789* | (2017.01) |
| *A61K 8/86* | (2006.01) |
| *A61Q 19/08* | (2006.01) |

(52) U.S. Cl.
CPC ............. *A61K 8/983* (2013.01); *A61K 8/14* (2013.01); *A61K 8/64* (2013.01); *A61K 8/86* (2013.01); *A61K 8/9789* (2017.08); *A61Q 19/08* (2013.01)

(58) Field of Classification Search
CPC ...................................... A61K 9/127
See application file for complete search history.

(56) References Cited

U.S. PATENT DOCUMENTS

| | | | |
|---|---|---|---|
| 2002/0161017 A1* | 10/2002 | Achari | A61K 9/0043 514/289 |
| 2003/0013753 A1* | 1/2003 | Aung-Din | A61K 47/14 514/419 |
| 2011/0008458 A1* | 1/2011 | Gandy | A61P 17/02 424/530 |
| 2014/0357731 A1 | 12/2014 | Needleman | |

FOREIGN PATENT DOCUMENTS

| | | | |
|---|---|---|---|
| AU | 642784 B2 | 5/1992 | |
| JP | 2014172899 A | 9/2014 | |
| WO | WO2011101760 A1 | 8/2011 | |
| WO | WO-2014126931 A1 * | 8/2014 | ........... A61K 31/133 |
| WO | WO2015088663 A1 | 6/2015 | |
| WO | WO2016109655 A1 | 7/2016 | |

OTHER PUBLICATIONS

Garanina et al. (Blood, 2017, Supplement:4814, 4 pages).*
International Search Report and Written Opinion; dated Oct. 23, 2017 for PCT Application No. PCT/AU2017/000158.
International Preliminary Report on Patentability; dated Feb. 5, 2019 for PCT Application No. PCT/AU2017/000158.
Novo Solutions MD, Moisturizing Renewal Cream SPF 15; Mintel Global New Products Database Record ID: 1617499; published Aug. 2011.
Esthe Pro Labo, U-Cord Cream Pro; Mintel Global New Products Database Record ID: 1516471; Published Jan. 2011.

* cited by examiner

*Primary Examiner* — Kyle A Purdy
(74) *Attorney, Agent, or Firm* — Mendelsohn Dunleavy, P.C.

(57) ABSTRACT

There is provided a formulation for skin rejuvenation comprising lyophilised umbilical cord plasma comprising at least one active chemokine, at least one growth factor and at least one cytokine; a transdermal carrier; and a liposomal base, wherein at least a portion of the lyophilised umbilical cord plasma and transdermal carrier are contained within liposomes of the liposomal base. There is also provided a dosage form for skin rejuvenation comprising 1-5% (w/w) lyophilised umbilical cord plasma comprising at least one active chemokine, at least one growth factor and at least one cytokine; 85-95% (w/w) polyethylene glycol; and 0.1-2% (w/w) gum acacia.

19 Claims, 10 Drawing Sheets

(A)

(D)

SKIN CARE FORMULATION

RELATED APPLICATIONS

This application claims the benefit of U.S. Provisional Patent Application No. 62/369,240, filed on 1 Aug. 2016 the disclosure of which is hereby expressly incorporated by reference in its entirety.

TECHNICAL FIELD

The technology relates to lyophilised plasma derived from umbilical cord blood, methods for its production, and methods for its use in skin care. In particular, the lyophilised plasma comprises active growth factors, chemokines and cytokines.

BACKGROUND

Human skin is subject to deterioration due to numerous factors including aging and dermatological disorders conditions or diseases such as dermatitis, psoriasis, eczma, pruritus, acne, rash, dryness and wounding. In addition, deterioration occurs from environmental factors such as from wind, air conditioning, and central heating, or through the normal ageing process, which may be accelerated by exposure of skin to sun. In particular, ageing is characterized by the appearance of wrinkles, variations in skin pigmentation and the loss of elasticity and compactness.

The pathogenesis of skin ageing is characterized by a decrease in collagen synthesis and an increase in collagen breakdown. The loss of dermal collagen is contributes to or facilitates wrinkling.

Numerous cosmetic and therapeutic skin care products are currently available for topical use to reduce the effects of skin ageing, skin conditions or hair loss. These typically comprise various chemical components, polymers, oils, antioxidants and the like.

It is believed that biological factors that stimulate collagen production and cell growth in wound healing might provide benefits for ageing skin and such factors, including growth factors, peptide fragments, and other biologically active molecules have been incorporated into anti-aging cosmetics and therapeutics.

Blood plasma derived from adults is typically used as therapy for coagulopathies and acute hemorrhages. Therapeutic plasma requires storage at a temperature of −25° C. or below in order to maintain activity of the coagulation factors and other actives in the plasma and frozen plasma has a limited shelf life. Adult plasma does not have the same profile of growth factors and other biologically active molecules as umbilical cord plasma (which included plasma derived from placental blood).

Umbilical cord blood is a rich source of stem cells as well as growth factors, chemokines and cytokines, and is typically used to as a source of hematopoietic stem cells for treatment of various blood cancers, and for treating various blood disorders such as anemia, immune disorders, and metabolic disorders. However, cord blood plasma is not used therapeutically.

While the use of biological factors to treat aging skin is gaining favor there remains an unmet need for effective topical and oral formulations for the prevention and treatment of skin damage, wrinkles and other defects associated with aging or caused by environmental factors.

The present inventors have developed a lyophilised plasma derived from umbilical cord blood that retains active cytokines, chemokines and growth factors and which is useful for the treatment of ageing skin.

SUMMARY

In a first aspect there is provided a formulation for skin rejuvenation comprising:
  lyophilised umbilical cord plasma comprising at least one active chemokine, at least one growth factor and at least one cytokine;
  a transdermal carrier; and
  a liposomal base,
  wherein at least a portion of the lyophilised umbilical cord plasma and transdermal carrier are contained within liposomes of the liposomal base.

The lyophilised umbilical cord plasma may be present in an amount of 1%, 2%, 3%, 4%, 5%, 6%, 7%, 8%, 9%, 10%, 11%, 12%, 13%, 14%, 15%, 16%, 17%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80%.

The chemokine may be selected from the group comprising eotaxin, IP-10, MCP-1, MIP-1α, MIP-1β and RANTES. The growth factor may be selected from the group comprising VEGF, G-CSF, bFGF, TGF-β1, GDF-11 and PDGF-BB. The cytokine may be selected from the group comprising IL1-receptor agonist, IL-1β, IL-4, IL-6, IL-7, IL-8, IL-9, IL-10, IL12p70, IL-13, IL17A, GM-CSF, TNFα and IFN-γ.

In one embodiment the lyophilised umbilical cord plasma comprises:
  eotaxin, IP-10, MCP-1, MIP-1α, MIP-1β and RANTES; and
  VEGF, G-CSF, bFGF, TGF-β1, GDF-11 and PDGF-BB; and
  IL1-receptor agonist, IL-1β3, IL-4, IL-6, IL-7, IL-8, IL-9, IL-10, IL12p70, IL-13, IL17A, GM-CSF, TNFα and IFN-γ.

The active chemokine, growth factor or cytokine may be present in an amount from about 0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, or at least about 100 ng/g of the formulation.

The transdermal carrier may be selected from the group comprising isopropyl alcohol, dipropylene glycol methylether, butylated hydroxytoluene dipropylene glycol monomethyl-ether, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as *Aloe vera* derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, vesicular aggregates, ethosomes, azone, castor oil derivatives, such as ethoxylated castor oil, jojoba oil derivatives, corn oil derivatives, propylene glycol, and emu oil derivatives.

The transdermal carrier may be present in an amount of 1% (w/w) 2% (w/w), 3% (w/w), 4% (w/w), 5% (w/w), or 6%, 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29% (w/w), 30% (w/w), 29% (w/w), 30% (w/w), 31% (w/w), 32% (w/w), 33% (w/w), 34% (w/w), 35% (w/w), 36% (w/w), 37% (w/w), 38% (w/w), 39% (w/w), 40% (w/w), 41% (w/w), 42% (w/w), 43% (w/w), 44% (w/w), 45% (w/w), 46% (w/w), 47% (w/w), 48% (w/w), 49% (w/w), or 50% (w/w).

The liposomal base may be an emulsion including a lipophilic component and an aqueous component.

In one embodiment the liposomal base is a mixture of about 60-80% wt/wt water, glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, *Aloe vera, tocopheryl acetate, prunus amygadalus amara kernel oil, Vitis vinifera* seed extract, *Triticum vulgare* germ oil, retinyl palmitate, ascorbyl palmitate, Pro-Lipo Multi-emulsion Liposomic System, tetrasodium EDTA, phenoxyethanol, and sodium hydroxymethylglycinate.

The formulation may further comprising a transdermal enhancer.

The transdermal enhancer may be selected from the group comprising ethyl alcohol, isopropyl alcohol, butyl alcohol, benzyl alcohol, ethylene glycol, diethylene glycol, propylene glycol, dipropylene glycol trimethylene glycol, glycerin, sorbitol, polyethylene glycol, polyoxyethylene-4-lauryl ether, polyoxyethylene-2-oleyl ether, polyoxyethylene-10-oleyl ether, cotton seed oil, corn oil, safflower oil, olive oil, castor oil, squalene, lanolin; propyl oleate, decyl oleate, isopropyl palmitate, glycol palmitate, glycol laurate, dodecyl myristate, isopropyl myristate, glycol stearate, oleyl alcohol, oleamide, dimethyldecylphosphoxide, methyloctylsulfoxide, dimethyllaurylamide, dodecylpyrrolidone, isosorbitol, dimethylacetonide, dimethylsulfoxide, decylmethylsulfoxide, dimethylformamide; salicylic acid; benzyl nicotinate; lauryl sulfate, sorbitol, polysorbate, linoleic acid, triacetin, ascorbic acid, panthenol, butylated hydroxytoluene, tocopherol, tocopherol acetate, and tocopheryl linoleate.

In one embodiment the formulations comprises:
a. 1 to 80% (v/w) of the lyophilized plasma;
b. 1% to 50% (w/w) of the transdermal carrier; and
c. up to 80% (w/w) of the liposomal base.

The formulation may be in a nasal dosage form or an oral dosage form selected from the group comprising a sublingual troche, tablet, wafer, lozenge, buccal troche, tablet, wafer, lozenge, and orally disintegrating tablet.

In a second aspect there is provided a dosage form for skin rejuvenation comprising:
d. 1-5% (w/w) lyophilised umbilical cord plasma comprising at least one active chemokine, at least one growth factor and at least one cytokine;
e. 85-95% (w/w) polyethylene glycol; and
f. 0.1-2% (w/w) gum acacia.

The chemokine may be selected from the group comprising eotaxin, IP-10, MCP-1, MIP-1α, MIP-1β and RANTES. The growth factor may be selected from the group comprising VEGF, G-CSF, bFGF, TGF-β1, GDF-11 and PDGF-BB. The cytokine may be selected from the group comprising IL1-receptor agonist, IL-1β, IL-4, IL-6, IL-7, IL-8, IL-9, IL-10, IL12p70, IL-13, IL17A, GM-CSF, TNFα and IFN-γ.

In one embodiment the lyophilised umbilical cord plasma comprises:
g. eotaxin, IP-10, MCP-1, MIP-1α, MIP-1β and RANTES; and
h. VEGF, G-CSF, bFGF, TGF-β1, GDF-11 and PDGF-BB; and
i. IL1-receptor agonist, IL-1β, IL-4, IL-6, IL-7, IL-8, IL-9, IL-10, IL12p70, IL-13, IL17A, GM-CSF, TNFα and IFN-γ.

The dosage form may further comprise a transdermal enhancer.

The lyophilised umbilical cord plasma may be present in an amount of 1%, 2%, 3%, 4%, 5%, 6%, 7%, 8%, 9%, 10%, 11%, 12%, 13%, 14%, 15%, 16%, 17%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, or 80% (w/w).

Any one of the active chemokine, growth factor or cytokine may be present in an amount from about 0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, or at least about 100 ng/g of dosage form.

The dosage form may contain about 0.1 mg, 0.5 mg, 1.0 mg, 5 mg, 10 mg, 15 mg, 25 mg, 35 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg 240 mg, 245 mg, or 250 mg of lyophilised plasma per dosage form.

The dosage form may be an oral dosage form selected from the group comprising a sublingual troche, tablet, wafer, lozenge, buccal troche, tablet, wafer, lozenge, and orally disintegrating tablet.

In a third aspect there is provided a method of treating, preventing or ameliorating a symptom or sign of a skin defect, the method comprising administering to a subject in need thereof a formulation of the first aspect or a dosage form of the second aspect.

The dosage form or formulation may be administered at least once per day.

The skin defect may be selected from the group comprising poor skin texture, wrinkles, fine lines, UV induced skin damage, skin aging, dry skin, hair follicle deterioration, alopecia, dermatitis, eczema, rash, pruritus, sun burn, burns, stretch marks, acne scars, and surgical scars.

The skin defect may be wrinkles or fine lines and the treatment reduces the number of wrinkles or fine lines by up to 5%, 10%, 20%, 30%, 40% or at least 50% compared to the number of wrinkles or fine lines before treatment.

In a fourth aspect there is provided a method for preparing lyophilised cord plasma comprising active cytokines, growth factors and chemokines, the method comprising:

a) maintaining frozen cord plasma at −35° C. to −55° C. for 350 to 550 minutes at a vacuum of under a vacuum of 50 to 250 microBar;

b) maintaining the temperature at 5-20° C. higher than in step a) for 50-150 minutes at 50-150 microBar c) maintaining the temperature at 5-10° C. higher than in step b) for 450-600 minutes at 50-150 microBar d) maintaining the temperature at 5-20° C. higher than in step c) for 300-500 minutes at 50-150 microBar d) raising the temperature to at 10-25° C. higher than in step d) over 250-350 minutes at 50-150 microBar e) maintaining the temperature used in step d) for 200-300 minutes at 50-150 microBar f) raising the temperature to about 0° C. over 50-150 minutes at 50-150 microBar g) maintaining the temperature at about 0° C. for 400-800 minutes at 50-150 microBar; and h) raising the temperature to 20° C. over 800-1500 minutes at 50-100 microBar.

In a fifth aspect there is provided a method for preparing lyophilised cord plasma comprising active cytokines, growth factors and chemokines, the method comprising:

a) maintaining frozen cord plasma at −45° C. for at least 480 minutes at a vacuum of 150 microBar;

b) maintaining the temperature at −35° C. for 100 minutes at 100 microBar c) maintaining the temperature at −30° C. for 570 minutes at 100 microBar d) maintaining the temperature at −25° C. for 390 minutes at 100 microBar d) raising the temperature to −10° C. over 300 minutes at 100 microBar e) maintaining the temperature at −10° C. for 240 minutes at 100 microBar f) raising the temperature to 0° C. over 100 minutes at 100 microBar g) maintaining the temperature at 0° C. for 630 minutes at 100 microBar; and h) raising the temperature to 20° C. over 1200 minutes at 70 microBar.

In a sixth aspect there is provided the lyophilised cord plasma produced by the method of the fourth or fifth aspect.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

DESCRIPTION

Figure 1:
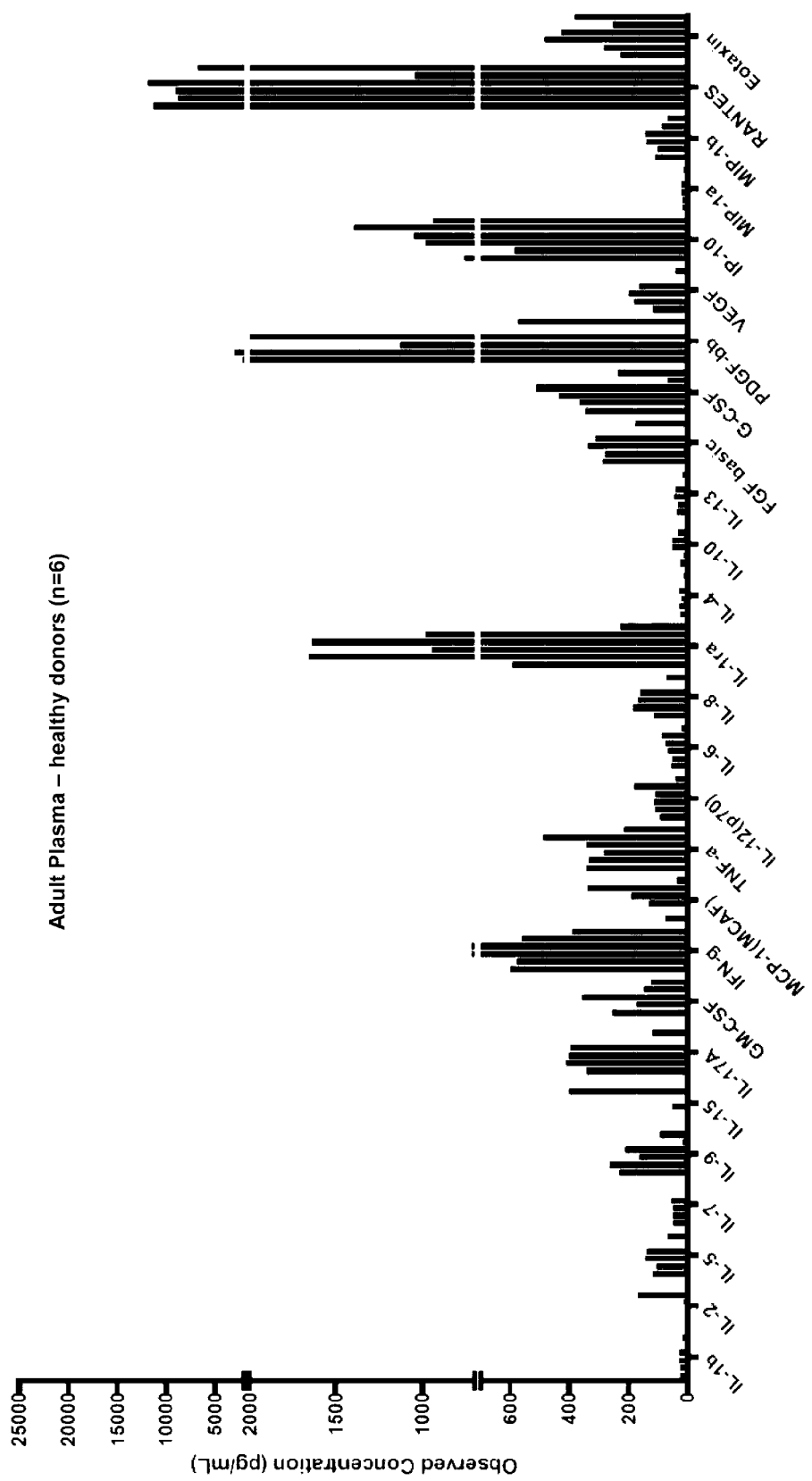
FIG. 1: Cytokine profile of healthy adult human plasma
Figure 2:
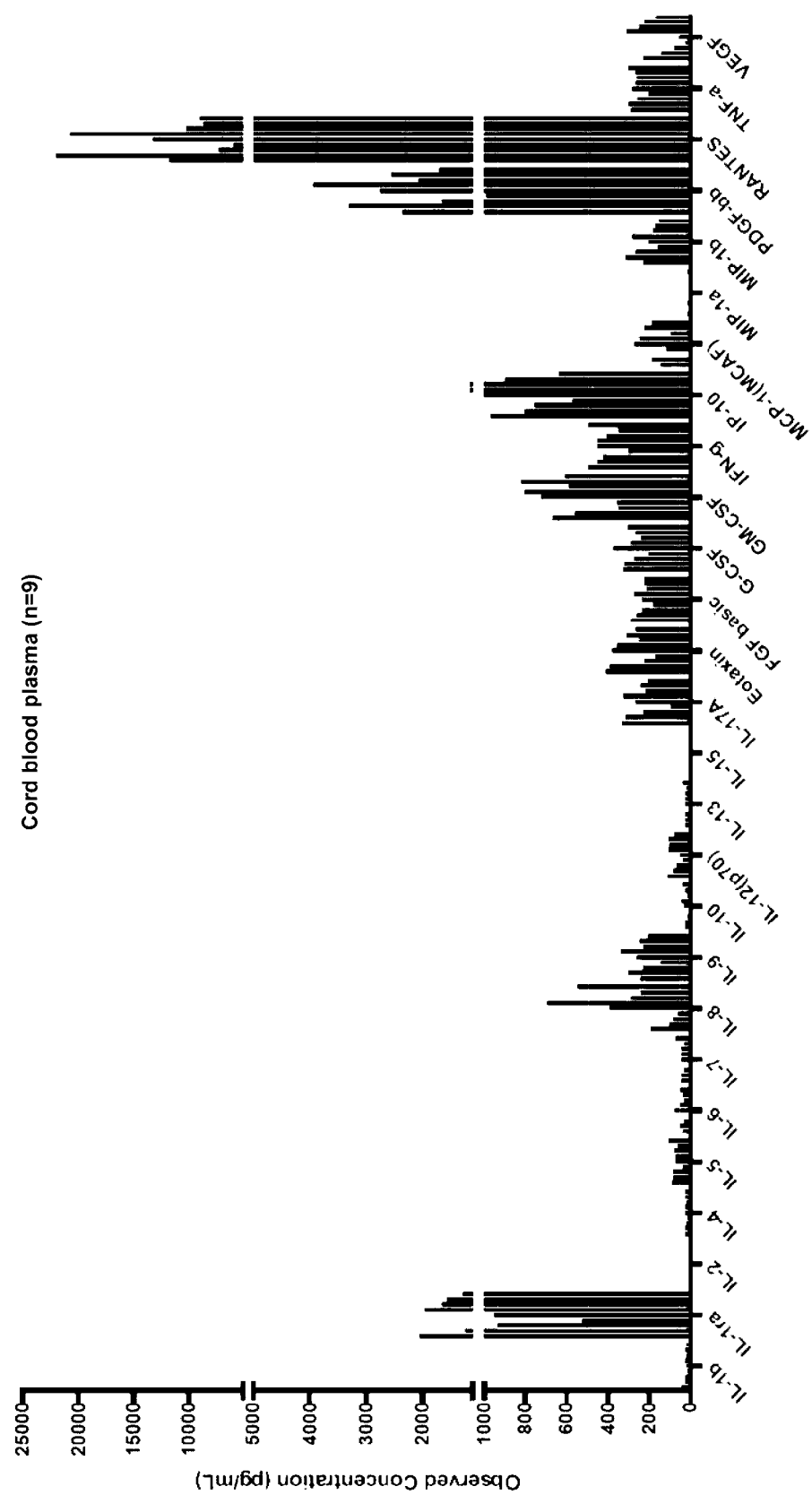
FIG. 2: Cytokine profile of individual cord blood plasma
Figure 3:
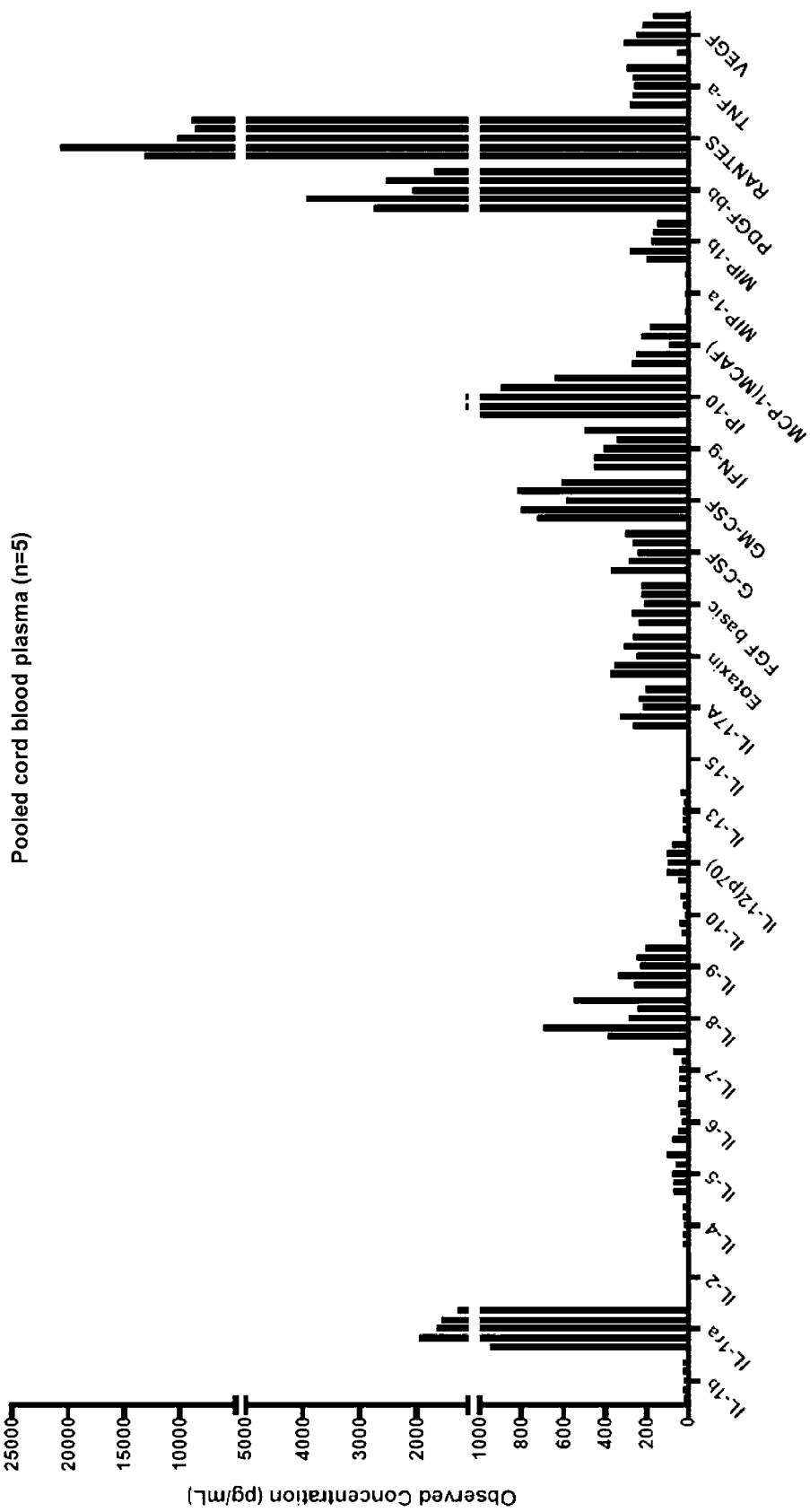
FIG. 3: Cytokine profile of blood group matched and pooled cord blood plasma
Figure 4:
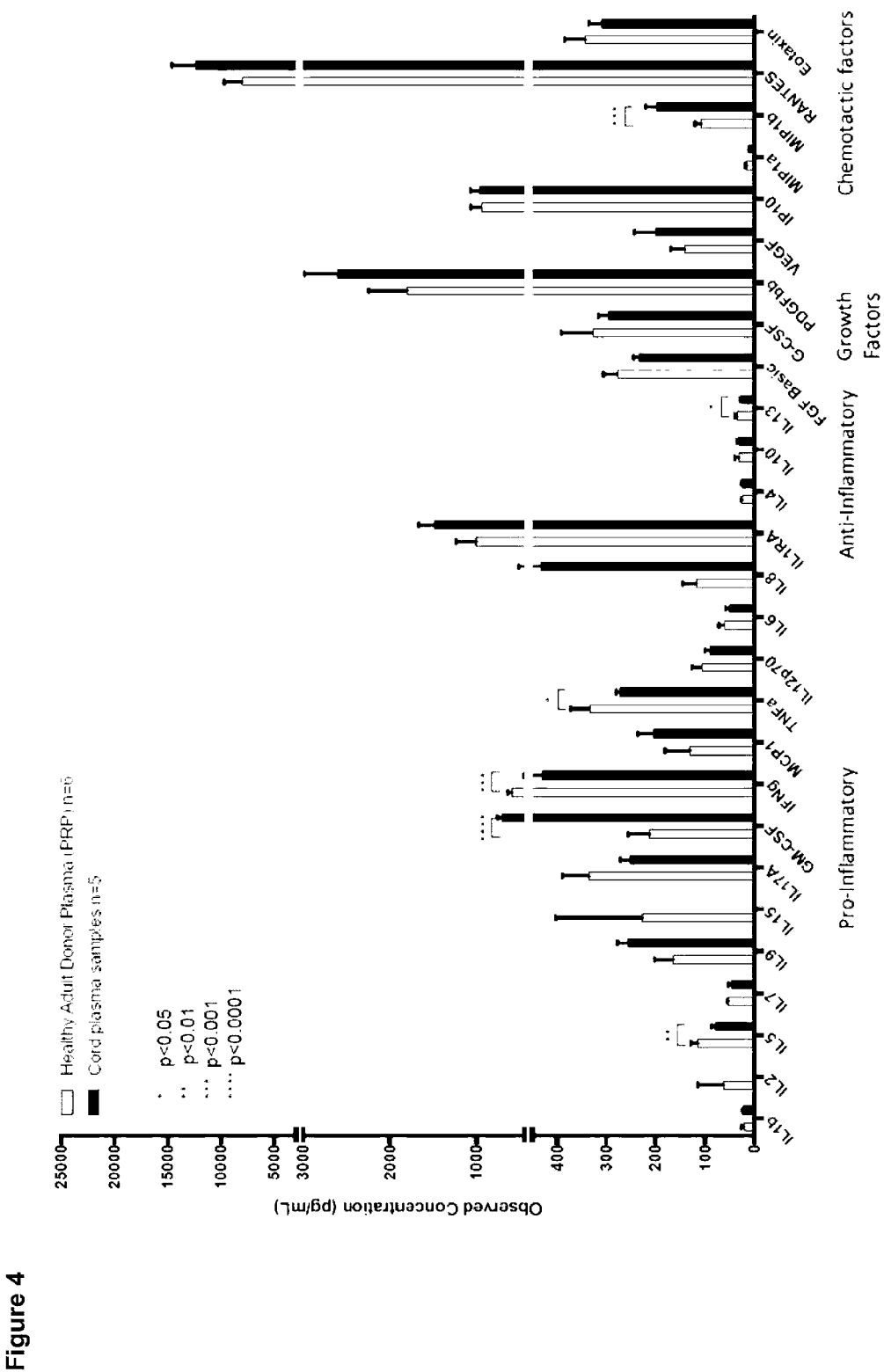
FIG. 4: Cytokine profile of healthy adult human plasma and cord blood plasma showing significant differences in levels of IL-5, IL-15 (not detected cord blood plasma), GMCSF, IFNγ, TNFα, IL-13 and MIP1b.
Figure 5:
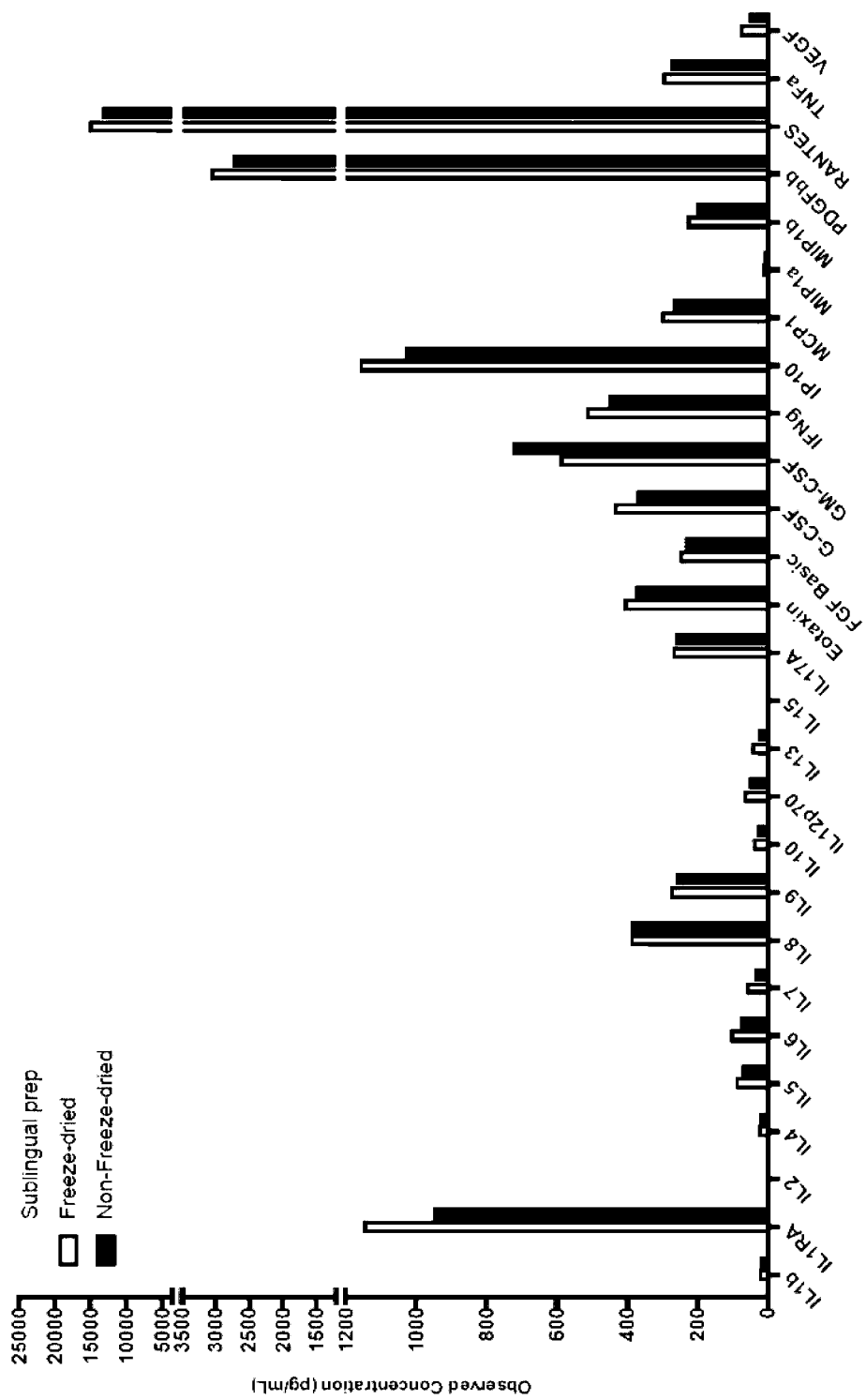
FIG. 5: Cytokine profile of sublingual troche of Example 6, lyophilised and reconstituted cord blood plasma and cord blood plasma

The present inventors have developed a lyophilised cord blood plasma product that retains active cytokines, growth factors and chemokines. In some aspects the lyophilized plasma can be formulated for delivery of one or more components of the luophilisedplasma across the oral mucosa. In other aspects the lyophilised plasma can be formulated for topical application for transdermal delivery of one or more components of the plasma. In some embodiments the component is systemically administered via the transdermal route.

Lyophilised Umbilical Cord Plasma

The formulations described herein contain lyophilised plasma. The source of the blood used to prepare the lyophilised cord blood plasma may be umbilical cord blood or blood retrieved from a placenta from a normal or C-section childbirth delivery. Alternatively or in addition the source of the blood can be blood donated to blood banks or from frozen cord blood units stored in public or family cord blood banks. The terms 'cord blood' and 'cord blood plasma' refer to blood or plasma, respectively from any or all of these sources.

The blood may be pooled from a number of donors. For example blood from individual donors may be typed, cross-matched or both and pooled according to type and or cross-matching characteristics before preparation of plasma from the pooled samples. The blood may be pooled from adult donors or from umbilical cords or placentas. Typically the umbilical cord blood is human umbilical cord blood.

Lyophilisation typically includes four steps, pre-treatment, freezing, primary and secondary drying. The pre-treatment step may include concentrating the plasma, the addition of stability enhancers or preservatives or increasing the surface area of the plasma.

In the second step (freezing) the plasma is cooled to below its triple point (the lowest temperature at which the solid and liquid phases coexist) in order to ensure that sublimation occurs in the drying steps. In some embodiments the freezing step includes annealing in which the temperature is reportedly raised and lowered. In other embodiments freezing is done as rapidly as practical to lower the plasma to below its eutectic point quickly to avoid ice crystal formation. Usually, the freezing temperature is between −30° C. and −90° C.

For example the plasma may be frozen at −30° C., −31° C., −32° C., −32° C., −33° C., −34° C., −35° C., −35° C., −36° C., −37° C., −38° C., −39° C., −40° C., −41° C., −42° C., −43° C., −43° C., −44° C., −45° C., −46° C., −47° C., −48° C., −49° C., −50° C., −51° C., −52° C., −53° C., −54° C., −55° C., −56° C., −57° C., −58° C., −59° C., −60° C., −61° C., −62° C., −63° C., −64° C., −65° C., −66° C., −67° C., −68° C., −69° C., −70° C., −71° C., −72° C., −73° C., −74° C., −75° C., −76° C., −77° C., −78° C., −79° C., −80° C., −81° C., −82° C., −83° C., −84° C., −85° C., −86° C., −87° C., −88° C., −89° C., or −90° C. In some embodiments the freezing temperature is −30° C., −31° C., −32° C., −32° C., −33° C., −34° C., −35° C., −35° C., −36° C., −37° C., −38° C., −39° C., −40° C., −41° C., −42° C., −43° C., −43° C., −44° C., −45° C., −46° C., −47° C., −48° C., −49° C., or −50° C. In some embodiment's the freezing temperature is −35° C., −36° C., −37° C., −38° C., −39° C., −40° C., −41° C., −42° C., −43° C., −43° C., −44° C., −45° C., −46° C., −47° C., −48° C., −49° C., −50° C., for example −40° C., −41° C., −42° C., −43° C., −43° C., −44° C., −45° C., −46° C., −47° C., −48° C., −49° C., or −50° C.

During primary drying the pressure is lowered and enough heat is supplied to the plasma for the ice to sublime. The amount of heat necessary can be calculated by a skilled person with consideration of the plasma's latent heat of sublimation. Pressure on the plasma is controlled through the application of partial vacuum. Application of a vacuum increases the rate of sublimation. In the primary drying phase about 90-95% of the water in the plasma is sublimated.

The secondary drying phase removes unfrozen water from the plasma and is dependent on the plasma's adsorption isotherms. The temperature is raised higher than in the primary drying phase, and can even be above 0° C. in order to break physicochemical interactions between water molecules and frozen material in the plasma. In some embodiments the pressure on the plasma is further decreased to facilitate desorption of water. The residual water content of the plasma is around 1% to 5%, for example 0.5%, 1%, 1.5%, 2.0%, 2.5%, 3.0%, 3.5%, 4.0%, 4.5% or about 5%.

The preparation of lyophilised cord plasma comprising active cytokines, growth factors and chemokines comprises multiple steps and begins with frozen plasma.

Typically, the first step of producing the lyophilised cord plasma requires that frozen plasma is maintained at around −35° C. to −55° C. for at least 350 to 550 minutes under a vacuum of 50 to 250 microBar. Following this there is a series of steps where the temperature of the plasma is gradually raised while the vacuum is maintained. For example the second step may include maintaining the temperature at 5-20° C. higher than the first step for 50-150 minutes at 50-150 microBar. The third step may include maintaining the temperature at 5-10° C. higher than in the second for 450-600 minutes at 50-150 microBar. The fourth step may include maintaining the temperature at 5-20° C. higher than in the third step for 300-500 minutes at 50-150 microBar. In the fifth step the temperature may be raised 10-25° C. higher than the fourth step over 250-350 minutes at 50-150 microBar, this temperature can them be maintained for 200-300 minutes at 50-150 microBar. In the sixth step the temperature may be raised to about 0° C. over 50-150 minutes at 50-150 microBar and this temperature is maintained for 400-800 minutes at 50-150 microBar; and finally, the temperature is raised to about 20° C. for 800-1500 minutes at 50-100 microBar.

Any variation of the above method can be used to produce lyophilised cord plasma comprising active cytokines, growth factors and chemokines One example of this general method is as follows:
a) maintaining frozen cord plasma at −45° C. for at least 480 minutes at a vacuum of 150 microBar;
b) maintaining the temperature at −35° C. for 100 minutes at 100 microBar
c) maintaining the temperature at −30° C. for 570 minutes at 100 microBar
d) maintaining the temperature at −25° C. for 390 minutes at 100 microBar
d) raising the temperature to −10° C. over 300 minutes at 100 microBar
e) maintaining the temperature at −10° C. for 240 minutes at 100 microBar
f) raising the temperature to 0° C. over 100 minutes at 100 microBar
g) maintaining the temperature at 0° C. for 630 minutes at 100 microBar; and
h) raising the temperature to 20° C. over 1200 minutes at 70 microBar In one embodiment, the lyophilised plasma may be formulated as a poultice, ointment, paste, cream, solution, suspension, emulsion, lotion, liniment, gel, hydrogel, hydrocolloid, foam, spray, powder, or any combination thereof.

The lyophilised plasma can be present in a formulation in an amount from about 1% to about 80% (w/w) or (v/v). For example the blood product can be present in a formulation in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%.

The lyophilised plasma contains one or more components such as metabolites, amino acids, proteins, growth factors, hormones, trace elements, vitamins and minerals.

For example the component may be selected from acetoacetate, acetone, acetylcholine, adenosine triphosphate, adrenocorticotrophic hormone, alanine, albumin, aluminum, aldosterone, amino acids, alpha-aminobutyric acid, d-aminolevulinic acid, ammonia nitrogen, cAMP, androstenedione, androsterone, angiotensin I, angiotensin II, alpha 1-antitrypsin, arginine, arsenic, ascorbic acid (vitamin C), aspartic acid, aspartic acid (in WBCs), bicarbonate, bile acids, bilirubin, biotin (vitamin H), bradykinin, bromide, cadmium, calciferol (vitamin D2), calcitonin (CT), calcium, carbon dioxide, carboxyhemoglobin (as HbCO), carcinoembryonic antigen, beta-carotene, carotenoids, cephalin, ceruloplasmin, cholecalciferol (vitamin D3), cholecystokinin (pancreozymin), cholesterol, choline, chorionic gonadotropin, citric acid, citrulline, coagulation factors (such as fibrinogen, prothrombin, tissue thromboplastin, proaccelerin, proconvertin, antihemophilic factor, christmas factor, stuart factor, plasma thromboplastin antecedent (zymogen form of factor XI), Hageman factor, fibrin-stabilizing factor, fibrin split products, Fletcher factor, Fitzgerald factor and von Willebrand factor), cobalamin (vitamin B12), Cocarboxylase, complement system (including C1q, C1r, C1s, C2, C3, factor B (C3 proactivator), C4 (b1E-globulin), C4 binding protein, C5 (b1F-globulin), C6, C7, C8, C9 and properdin), compound S, copper, corticosteroids, corticosterone, cortisol, c-peptide, c-reactive protein, creatine, creatinine, cysteine, dehydroepiandrosterone (DHEA), DHEA sulfate, DHEA sulfate, 11-deoxycortisol, dihydrotestosterone (DHT), diphosphoglycerate (phosphate), DNA, dopamine, enzymes, epidermal growth factor (EGF), epinephrine, ergothioneine, erythrocytes and fragments thereof, erythropoietin, estradiol (E2), estriol (E3), estrogen, estrone (E1), fat, free fatty acids, fatty acids, ferritin, alpha-1-fetoprotein, flavin adenine dinucleotide, fluoride, folate, folic acid, fructose, furosemide glucuronide, galactose, gastric inhibitory peptide (GIP), gastrin, globulin, alpha-1-globulin, alpha-2-globulin, beta globulin, gamma globulin, glucagon, glucosamine, glucose, glucuronic acid, glutamic acid, glutamine, glutathione, reduced, glycerol, glycine, glycogen, glycoprotein, cgmp, gonadotropin-releasing hormone, guanidine, haptoglobin, hemoglobin, hexosephosphate p, histamine, histidine, beta-hydroxybutyric acid, 17-hydroxycorticosteroids, 17-hydroxyprogesterone, antibodies (including immunoglobulin A, immunoglobulin D, iImmunoglobulin G, immunoglobulin M and immunoglobulin E), indican, inositol, insulin, insulin-like growth factor, iodine, iron, isoleucine, ketone bodies, alpha-ketonic acids, lactate, lecithin, leptin, leucine, leukocytes and fragments thereof (including neutrophil granulocytes, neutrophils, eosinophil granulocytes, eosinophils, basophil granulocytes, basophils, lymphocytes, monocytes and phagocytes), lipase p, lipids, lipoproteins, lithium, lysine, lysozyme (muramidase), alpha 2-macroglobulin, magnesium, malic acid, manganese, melatonin, methemoglobin, methionine, methyl guanidine, beta-2-microglobulin, MIP-1a, MIP-1b, mucopolysaccharides, mucoproteins, nerve growth factor (NGF), niacin, norepinephrine, nucleotides, ornithine, oxalate, oxytocin, pancreatic polypeptide, pantothenic acid (vitamin B5), para-aminobenzoic acid, parathyroid hormone (PTH), pentose, phenylalanine, phospholipid, phosphatase, phosphorus, phytanic acid, platelets or fragments thereof, platelet-derived growth factor, polysaccharides, potassium, pregnenolone, progesterone, proinsulin, prolactin, proline, prostaglandin, protein, protoporphyrin, prostate specific antigen, pseudoglobulin I, pseudoglobulin ii, purine, pyrimidine nucleotides, pyridoxine (vitamin B6), pyruvic acid, RANTES, relaxin, retinol (vitamin A), riboflavin (vitamin B2), RNA, secretin, serine, serotonin (5-hydroxytryptamine), silicon, sodium, somatotropin (growth hormone), sphingomyelin, succinic acid, sulfates, sulfur, taurine, testosterone, thiamine, thiocyanate, threonine, thyroglobulin (Tg), thyroid hormones, thyrotropin-releasing hormone, thyroxine (FT4), thyroxine-binding prealbumin, thyroxine-binding globulin, tin, alpha-tocopherol (vitamin e), transcortin, transferrin, triglycerides, triiodothyronine, tryptophan, tyrosine, urea, uric acid, valine, vasointestinal peptide (vip), vasopressin, zinc and any combination thereof.

The component may be a growth factor, cytokine, chemokine, hormone, vitamin, or cell fragment.

The growth factor may be selected from the group consisting of endothelial growth factor (EGF), hepatocyte growth factor (HGF), basic fibroblast growth factor (bFGF), granulocyte colony-stimulating factor (G-CSF), vascular endothelial growth factor (VEGF), transforming growth factor alpha (TGF-α), TGF-β1, TGF-β2, TGF-β3, platelet-derived growth factor (PDGF)-AA, PDGF-AB, PDGF-BB, insulin-like growth factor-1 (IGF-1), BMP, BDNF, EGF, HGF, PDGF, FGF, PGF, GDF-8, NGF, Epo, TPO, TCGF, IGF-I, IGF-II, KGF, VEGF, and any combination thereof.

The cytokines may be pro-inflammatory or anti-inflammatory.

The proinflammatory cytokine may be for example granulocyte-macrophage colony-stimulating factor (GM-CSF), interleukin (IL)-1α, IL-1β, IL-2, IL-2R, IL-3, IL-4, IL-6, IL-7, IL-8, IL-9, IL-10, IL-11, IL-12, IL-12p40, IL12p70, IL-13, IL-14, IL-15, IL-17, IL17A, tumour necrosis factor (TNF)α, TNF-β, interferon (IFN)-α, INF-β, INF-γ or any combination thereof.

The anti-inflammatory cytokine may be for example IL-1RA, IL-4, IL-5, IL-10, IL-13, IFNα or any combination thereof.

The chemokine may be eotaxin, protein 10 (IP-10), monocyte chemoattractant protein-1 (MCP-1), IFNγ-induced monokine, macrophage inflammatory protein (MIP)-1α, MIP-1β, RANTES or any combination thereof.

The cytokines may be isolated from the blood product. For example the cytokine

In some embodiments the cytokines are freeze dried or lyophilised. These methods are well known in the art and are commonly used to preserve the function of temperature sensitive products, such as enzymes and blood products like cytokines.

The hormone may be selected from the group consisting of an amino acid hormone, eicosanoid hormone, a peptide hormone and a steroid hormone.

The amino acid hormone may be selected from the group consisting of epinephrine, melatonin, triiodothyronine and thyroxine.

The eicosanoid hormone may be selected from the group consisting of prostaglandins, leukotrienes, prostacyclin and thromboxane.

The peptide hormone may be selected from the group consisting of amylin, anti-mullerian hormone, adiponectin, angiotensinogen, angiotensin, vasopressin, atrial natriuretic peptide, brain natriuretic peptide, calcitonin, cholecystokin, corticotropin-releasing hormone, cortistatin, encephalin, endothelin, erythropoietin, galanin, gastric inhibitory peptide, gastrin, ghrelin, glucagon, glucagon-like-peptide-1, gonadotropin-releasing hormone, growth hormone-releasing hormone, hepcidin, human chorionic gonadotropin, human placental lactogen, human growth hormone, inhibin, insulin, insulin-like growth factor, leptin, lipotropin, melanocyte stimulating hormone, motilin, orexin, oxytocin, pancreatic polypeptide, parathyroid hormone, pituitary adenylate cyclase-activating peptide, prolactin, prolactin releasing hormone, relaxin, renin, secretin, somatostatin, thrombopoietin, thyroid-stimulating hormone and vasoactive intestinal peptide.

The steroid hormone may be selected from the group consisting of testosterone, dehydroepiandrosterone, androstenedione, dihydrotestosterone, aldosterone, estradiol, estrone, estriol, cortisol, progesterone, calcitriol and calcidiol.

In some embodiments the lyophilised umbilical cord blood plasma comprises at least one active chemokine, growth factor and cytokine The cytokine may be selected from the group comprising: IL1-receptor agonist, IL-1β, IL-4, IL-6, IL-7, IL-8, IL-9, IL-10, IL12p70, IL-13, IL17A, GM-CSF, TNFα and IFN-γ.

The chemokine may be selected from the comprising eotaxin, IP-10, MCP-1, MIP-1α, MIP-1β and RANTES.

The growth factor may be selected from the group comprising VEGF, G-CSF, bFGF, GDF-11, TGF-β1 and PDGF-BB.

In some embodiments the lyophilised plasma comprises IL1-receptor agonist, IL-1β, IL-4, IL-6, IL-7, IL-8, IL-9, IL-10, IL12p70, IL-13, IL17A, TNFα, IFN-γ, eotaxin, IP-10, MCP-1, MIP-1α, MIP-1β, RANTES, VEGF, G-CSF, GM-CSF, bFGF, GDF-11, TGF-β1 and PDGF-BB.

In some embodiments each component may be present in an amount from about 0.1-1000 pg/mg, about 1-1000 pg/mg, about 50-1000 pg/mg, about 100-1000 pg/mg, about 200-1000 pg/mg, about 300-1000 pg/mg, about 400-1000 pg/mg, about 500-1000 pg/mg, about 600-1000 pg/mg, about 700-1000 pg/mg, about 800-1000 pg/mg, about 900-1000 pg/mg, about 1-100 ng/mg, about 10-100 ng/mg, about 10-100 ng/mg, about 20-100 ng/mg, about 30-100 ng/mg, about 40-100 ng/mg, about 50-100 ng/mg, about 60-100 ng/mg, about 170-100 ng/mg, about 80-100 ng/mg, about 90-100 ng/mg, or at least about 100 ng/mg of lyophilised plasma.

In some embodiments each component may be present in an amount from about 0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, or at least about 100 ng/g of lyophilised plasma.

Dosage Forms

In some aspects the lyophilised plasma is present in an oral dosage form selected from the group consisting on of a sublingual troche, tablet, wafer or lozenge. In some embodiments the dosage form is a buccal troche, tablet, wafer, lozenge or orally disintegrating tablet.

In some embodiments the oral dosage form is solid at room temperature. Preferably the oral dosage form at least partially dissolves at body temperature within the mouth of a user.

The oral dosage form (e.g. sublingual troche) troche can be prepared using any method known in the art. For example the sublingual troche may be prepared by combining low molecular weight polyethylene glycol (for example with molecular weights of 1300 to 1650 g/mol) with gum acacia, citric acid, a sweetener such as stevia extract powder, and a flavoring such as peppermint oil with the lyophilised plasma. For example the lyophilised plasma can be from typed and/or cross matched donors.

In some aspects the oral dosage form is for direct application to the buccal, lingual, or sublingual area. For example, when applied lingually or sublingually, the dosage form stimulates saliva production, thus enhancing rapid disintegration of the dosage form and dissolution of the lyophilised cord blood plasma. When applied sublingually, the dosage form is applied directly to the absorptive membrane on the underside of the tongue. For example, the dosage form may be in the form of a strip, oral mist, granulated particles, gum, lyophilized wafer/tablet, lozenge, pill, tablet, rapidly disintegrating tablet, troche, and the like. In some embodiments the dosage form includes a lozenge, wafer or troche.

The dosage forms can be manufactured using conventional processes. Actual methods of preparing such dosage forms are known, or will be apparent, to those skilled in this art. See, fro example Remington: The Science and Practice of Pharmacy, 20th Ed., (Lippincott, Williams and Wilkins Publishing).

For example, the preparation of an oral dosage from such as a troche typically involves combining lyophilized cord blood plasma with polyethylene glycol, (e.g. with approximate molecular weights of 1000-2000 g/mol) gum acacia together with sweeteners and/or flavors. Any known sweetener may be used, for example sugar, stevia, or aspartame. Examples of suitable flavors include peppermint, menthol, mint. The skilled person will be aware of other suitable sweeteners and flavors and will be aware of the appropriate amounts of each to use in a troce Assembly of the lozenge or troche comprises: (i) preparing a base of polyethylene glycol, gum acacia, stevia extract (or other suitable sweetener), by melting at normal atmospheric pressure; (ii) adding the desires amount of lyophilized plasma; (iii) adding desired flavorings; and (iv) adding the solution to a lozenge or troche mold device.

The lyophilized plasma is present in an amount of about 0.5% (w/w) to about 25% (w/w) of the dosage from such as a troche. For example the lyophilized plasma may be present in a troche in amount of 0.5, 1.0, 2, 3, 4, 5, 6, 7, 8,9, 10, 11, 12, 13, 14 15, 16, 17, 18, 19, 20, 21, 22, 23, 24, or about 25% (w/w). In some embodiment the troche comprises 1, 2, 3, 4, or 5% (w/w) lyophilized plasma.

The troches comprise 75-95% (w/w) polyethylene glycol, for example the troche comprises 75, 76, 77, 78, 79, 80, 81, 82, 83, 84, 85, 86, 87, 88, 89, 90, 91, 92, 93, 94, or about 95% (w/w) polyethylene glycol. Ion some embodiments the troche comprises 85, 86, 87, 88, 89 90, 91, 92, 93, 94 or 95% (w/w) polyethylene glycol.

The polyethylene glycol typically has an average molecular weight of 1000-5000 g/mol, for example the average molecular weight may be 1000, 1250, 1500, 1750, 2000, 2250, 2500, 2750, 3000, 3250, 3500, 3750, 4000, 4250, 4500, 4750 or 5000 g/mol.

The troche comprises gum acacia or gum arabic. The troches typically comprise 0.1 to 10% (w/w gum acacia. For example the troche may compromise 0.1, 0.5, 1, 2, 3, 4, 5, 6, 7, 8, 9, or 10% (w/w) gum acacia. In some embodiments the troche comprises 0.1, 0.25, 0.5, 0.75, 1.0, 1.25, 1.5, 1.75, or about 2.0% (w/w) gum acacia.

Each individual dosage form contains from about 0.1 mg to about 250 mg lyophilised cord blood plasma to be administered for at least partial transmucosal, i.e., buccal or sublingual, absorption is generally about. For example the amount of lyophilised cord blood plasma in each individual dosage from may be about 0.1 mg, 0.5 mg, 1.0 mg, 5 mg, 10 mg, 15 mg, 25 mg, 35 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg 240 mg, 245 mg, or 250 mg.

In some embodiments each component (i.e. each cytokine, growth factor and chemokine) may be present in the dosage form in an amount from about 0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, or at least about 100 ng/g of dosage form.

The dosing regimen can be modulated in order to achieve satisfactory therapeutic results.

The dosage form will generally contain from approximately 1% to about 80% by weight of lyophilised cord blood plasma. For example the lyophilised plasma can be present in a dosage form in an amount of about 1%, about 2%, about 3%, about 4%, about 5%, about 6%, about 7%, about 8%, about 9%, about 10%, about 11%, about 12%, about 13%, about 14%, about 15%, about 16%, about 17%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%.

In some embodiments the dosage form contains an orally disintegrating carrier, for example a bioerodible (hydrolyzable) polymeric carrier that may also serve to adhere the dosage form to the buccal and/or sublingual mucosa. The orally disintegrating carrier can be any such carrier known in the art. Generally, the orally disintegrating carrier may comprise hydrophilic (water-soluble and/or water-swellable) polymers that may adhere to a wet surface in the oral cavity. Polymeric carriers include, but are not limited to, acrylic acid polymers; hydrolyzed polyvinylalcohol; polyethylene oxides; polyacrylates; vinyl polymers; polyvinylpyrrolidone; dextran; guar gum; pectins; starches; or cellulosic polymers. Acrylic polymers include, but are not limited to, polymers known as "carbomers" (e.g., Carbopol®). Polyethylene oxides include, but are not limited to, Polyox® water soluble resins. Polyacrylates include Eudragit®. Cellulosic polymers include, but are not limited to, hydroxypropyl methylcellulose (e.g., Methocel®); hydroxypropyl cellulose (e.g., Klucel®); hydroxypropyl cellulose ethers; hydroxyethyl cellulose; carboxymethyl cellulose; sodium carboxymethyl cellulose; methyl cellulose; ethyl cellulose; cellulose acetate phthalate; cellulose acetate butyrate; microcrystalline cellulose; and the like. Conventional nontoxic solid carriers include, but are not limited to, at least one of pharmaceutical grades of mannitol, lactose, starch, magnesium stearate, sodium saccharin, talc, glucose, sucrose, or magnesium carbonate.

In some embodiments the dosage form includes a permeation enhancer in the formulation in order to increase the rate at which the lyophilised cord blood plasma permeates through the mucosal tissue to which it is applied, e.g., the buccal mucosa, lingual, or sublingual mucosa. These permeation enhancers also are referred to as accelerants, adjuvants, and absorption promoters, and are collectively referred to herein as "permeation enhancers." The permeation enhancer includes those compounds with diverse mechanisms of action including those which have the function of improving the solubility and diffusibility of the lyophilised cord blood plasma, and those which improve percutaneous absorption by changing the ability of the stratum corneum to retain moisture, softening the skin, improving the skin's permeability, acting as penetration assistants, or changing the state of the skin such as the boundary layer.

Suitable permeation enhancers include, but are not limited to, dimethylsulfoxide ("DMSO"), dimethyl formamide ("DMF"), N,N-dimethylacetamide ("DMA"), decylmethylsulfoxide ("C10MSO"), polyethylene glycol monolaurate ("PEGML"), glycerol monolaurate, lecithin, 1-substituted azacycloheptan-2-ones, alcohols, or surfactants. Surfactants include, but are not limited to, Tergitol®, Nonoxynol-9®, and TWEEN-80®. 1-Substituted azacycloheptan-2-ones include 1-n-dodecylcyclazacycloheptan-2-one (available under the trademark Azone®) or SEPA®).

Optionally other ingredients may be incorporated into the dosage form. The additional components include, but are not limited to, at least one of pH buffering agents, disintegrants, diluents, binders, emulsifying agents, lubricants, wetting agents, flavoring agents, colorants, preservatives, and the like. Additional components that may be incorporated into sublingual dosage forms are known, or will be apparent, to those skilled in this art. See, Remington: The Science and Practice of Pharmacy, 20th edition (Lippincott, Williams and Wilkins Publishing), p. 859.

Buffering agents include, but are not limited to, sodium acetate, sorbitan monolaurate, triethanolamine sodium acetate, or triethanolamine oleate Disintegrants include, but are not limited to, cross-linked polyvinylpyrrolidones {e.g., crospovidone, such as Polyplasdone® XL available from GAF); cross-linked carboxylic methylcelluloses {e.g., croscarmelose, such as Ac-di-sol® available from FMC); alginic acid, calcium silicate, and sodium carboxymethyl starches {e.g., Explotab® available from Edward Medell Co., Inc.); methylcellulose; agar bentonite; alginic acid; calcium carbonate; polyoxyethylene sorbitan fatty acid esters; sodium lauryl sulfate; stearic monoglyceride; or lactose.

Suitable diluents are those which are generally useful in pharmaceutical formulations prepared using compression techniques. Diluents include, but are not limited to, dicalcium phosphate dihydrate; sugars, including those that have been processed by co-crystallization with dextrin; lactose; calcium phosphate; cellulose; kaolin; mannitol; sodium chloride; dry starch; powdered sugar; and the like.

Binders are those compounds that enhance adhesion. Binders include, but are not limited to, water, ethanol, polyvinylpyrrolidone, starch, gelatin, or sugars. Sugars include sucrose, dextrose, molasses, and lactose. Lubricants include, but are not limited to, stearic acid, polyethylene glycol, or stearates, such as magnesium stearate. Wetting agents include, but are not limited to, glycerin, starches, and the like.

Conventional flavoring agents may be used, such as those described in Remington: The Science and Practice of Pharmacy, 20th Ed. (Lippincott, Williams and Wilkins Publishing), which is incorporated herein by reference. The pharmaceutical compositions of the invention generally contain from about 0 to 2% by weight of a flavoring agent.

Topical Formulations

The formulations include three components: a liposomal base, lyophilised cord plasma and a transdermal carrier.

The lyophilised cord plasma in the topical formulation is present in the aqueous and/or lipophilic portions but is also encapsulated in liposomes of the base. The liposomes have a lipophilic membrane surrounding an aqueous interior compartment. The structure of the liposomes may include multilamellar or unilamellar liposomes or unstructured liposomal aggregates and/or combinations of the same. A portion of the lyophilised plasma is present in the aqueous compartments of the liposome.

The topical formulations described herein are useful for preventing, reducing and/or eliminating skin defects such as poor skin texture, wrinkles, frown lines, UV induced skin damage, skin ageing, dry skin, hair follicle deterioration, alopecia, dermatitis, eczema, rash, psoriasis pruritus, sun burn, burns, stretch marks, acne scars and surgical scars (wound healing). Accordingly, the topical formulations may be used as an alternative or in addition to cosmetic surgery, injectable cosmetic treatments such as fillers (Hyaluronic Acid) BOTOX®, silicone or other products.

Skin ageing is a complex process characterized by decreased in collagen synthesis and increased collagen degradation. A number of growth factors stimulate collagen production. In some embodiments the lyophilised plasma used in the topical formulations contain growth and/or inflammatory mediators such as, for example, PDGF, IGFs, FGFs, TGFs, EGF, VEGF, HGF, IL-6, G-SCF and KGF as well as extracellular matrix proteins such as type I and type III collagens, fibronectin, terascin, glycosaminoglycans, versican, decorin and other secreted dermal matrix proteins, which may be useful in preventing or repairing skin defects. In addition peptides such as KTTKS and palmitoyl-KTTKS which promote collagen synthesis, and argireline, a synthetic peptide that inhibits muscle-induced wrinkling of the skin, may also be added to the formulation.

The topical formulations may include one of more of the following general types of ingredients:

Emollients: for example plant oils, mineral oils, shea butter, cocoa butter, petrolatum, cholesterol, silicones or animal oils (including emu, mink and lanolin). These emollients contribute to softening and smoothing the skin while functioning to assist in moisture retention. In some embodiments, jojoba, squalene and lanolin are used because of their similarity to and are the least comedogenic (pore-clogging).

Humectants: for example sorbitol, glycols, glycerins and sodium PCA. Humectants act to attract water to the skin and are desirable inclusions in the formulations for applications of the formulations to treat/prevent skin damaged by sun and dehydration.

Soothing agents and anti-irritants: for example bisabolol, allantoin, burdock root, aloe, licorice root, glycyrrhetinic acid, green tea and chamomile extract, may be added to the formulations.

Vitamins and antioxidants: for example vitamins A, B group (in particular vitamins B3, B5 and B9), C and E.

Alpha hydroxy acids (AHAs) and beta hydroxy acids (BHAs): these compounds are believed to be useful to clear pores and remove dead skin thereby promoting smoother, moister skin. Examples of useful AHAs formulations include glycolic acid and lactic acid, fruit or citrus acid, and sugarcane extracts. Examples of a useful BHA is salicylic acid. AHA increases sun sensitivity and so formulations containing AHA typically also include physical and/or chemical sunscreen agents.

Antioxidants: Suitable antioxidants include ascorbic acid, sodium sulfite, sodium metabisulfite, sodium bisulfite, sodium thiosulfite, sodium formaldehyde sulfoxylate, isoascorbic acid, thioglycerol, thiosorbitol, thiourea, thioglycolic acid, cysteine hydrochloride, 1,4-diazobicyclo-(2,2,2)-octane, butylated hydroxytoluene (BHT), ascorbyl palmitate, butylated hydroxyanisole, a-tocopherol, phenyl-a-naphthylamine, and mixtures thereof; and Polysaccharides such as glucomannan or guar gum.

In one embodiment the topical formulation comprises hyaluronic acid (HA) or a salt thereof. The HA or salt thereof may be present in an amount of 0.1% to 10% by weight of the topical formulation. For example the For example the HA or salt thereof may be present in the formulation at about 0.1% (w/w), about 0.5% (w/w), about 1% (w/w), about 2% (w/w), about 3% (w/w), about 4% (w/w), about 5% (w/w), about 6% (w/w), about 7% (w/w), about 8% (w/w), about 9% (w/w) or about 10% (w/w).

The topical formulations are topically applied to a subject for example by rubbing, smearing or massaging into an area of skin.

Assays commonly employed by those of skill in the art may be utilized to test the activity of the particular components, thereby ensuring that an acceptable level of biological activity (e.g., a therapeutically effective amount) is retained. Doses of such therapeutic factors are well known to those of skill in the art and may be found in pharmaceutical compendia such as the Physicians' Desk Reference, Medical Economics Data Publishers; Remington's Pharmaceutical Sciences, Mack Publishing Co.; Goodman & Gilman, The Pharmacological Basis Of Therapeutics, McGraw Hill Publ.

The effective doses of any of the components described herein may routinely be determined using techniques well known to those of skill in the art. A "therapeutically effective" dose refers to that amount of the component sufficient to result in amelioration of at least one sign or symptom of skin defect.

The topical formulations can have a pH of about 6 to about 9, in some embodiments the pH is from 6.0 to 7.0. In other embodiments the pH can be 1, 2, 3, 4, 5, 6, 7, 8, 9, 10, 11, 12, 13, or 14.

In some embodiments the topical formulations have UVA and UVB absorption properties. In these embodiments, the formulations have a sun protection factor (SPF) of 2, 3, 4, 5, 6, 7, 8, 9, 10, 11, 12, 13, 14, 15, 20, 25, 30, 35, 40, 45, 50, 55, 60, or more, or any integer or derivative therein. The topical formulation may comprise any UVA and UVB absorbing compound known in the art. For example the formulation may comprise oxybenzone, avobenzone, octisalate, octocrylene, homosalate, octinoxate, zinc oxide titanium dioxide or any combination thereof.

The topical formulation is applied topically and can be prepared in the form of a hand or body cream, hair shampoo, under eye cream, bath gel or soap, shaving or after shaving lotion. These forms can be prepared using the formulations described herein in conjunction within methods known in the art.

The topical formulations can provide systemic delivery via a transdermal route of at least one component of the lyophilised plasma. The component crosses the skin and enters the circulation (for example the blood or lymph) and is distributed substantially throughout the body (i.e. systemically). Accordingly, while the effect of the formulation will be observable at the site of administration (for example a portion of the skin) the effects will also be observable at sites distal to the site of administration due to the systemic delivery of one or more components of the lyophilised plasma.

Liposomal Base

Any suitable liposomal base known in the art may be used in the topical formulations provided herein. Typically the liposomal base is an emulsion that includes a lipophilic component and an aqueous component that are emulsified such that the lipophilic component forms liposomes containing a portion of the aqueous component.

The liposomal base may take any form. For example the liposomal base may be a lotion, a cream, a gel or a paste. Preferably the liposomal base is a lotion or a cream.

One example of a commercially available liposomal base suitable for use in the topical formulations provided herein includes, but is not limited to, LIPODERM™ cream or gel (a mixture of about 60-80% wt/wt water, with glycerin, C12-15 alkyl benzoate, glyceryl stearate, dimethicone, cetearyl alcohol, cetearyl glucoside, polyacrylamide, cetyl alcohol, magnesium aluminum silicate, xanthan gum, *Aloe vera* (aloe barbadensis), tocopheryl acetate (vitamin E acetate), prunus amygadalus amara (bitter almond) kernel oil, *Vitis vinifera* (Grape) seed extract, *Triticum vulgare* (wheat) germ oil, retinyl palmitate (vitamin A palmitate), ascorbyl palmitate (vitamin C palmitate), Pro-Lipo Multi-emulsion Liposomic System, tetrasodium EDTA, phenoxyethanol, sodium hydroxymethylglycinate). PCCA, Houston, Tex.

Other suitable liposomal bases include, but are not limited to, DEMI-GEL™ emulsion (which is a mixture of 4% lecithin isopropyl palmitate containing lecithin soya granular, isopropyl palmitate NF, sorbic acid NF).

Although use of commercially available liposomal bases, gels and diluents is convenient the formulations provided herein may be prepared with any suitable emulsion.

Transdermal Carriers and Enhancers

The topical formulations and dosage forms may comprise a transdermal carrier to facilitate passage of the component of the lyophilised plasma through the skin or oral mucosa. Preferably, the transdermal carrier facilitates passage of the component of the plasma or serum through the skin or oral mucosa and into the circulation to so that the component is administered systemically.

It is to be understood that any suitable transdermal carrier or solvent which facilitates transdermal absorption of the component may be used. Examples of suitable transdermal carriers include carriers such as isopropyl alcohol, dipropylene glycol methyl-ether, butylated hydroxytoluene dipropylene glycol monomethyl-ether, 1-methoxy 2-propanol (glysolv PM/Icinol PM), Ethylene glycol monobutylether (butyl glyxolv/butyl icinol), Butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, such as *Aloe vera* derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, Transfersomes® (IDEA AG). Transfersomes® are artificial vesicles designed to mimic a cell vesicle and deliver component into a cell. The bounding membrane of a Transfersomes® is more flexible than that of a liposome, allowing it to deform and pass through openings in a barrier, such as the skin, whose diameters are much smaller than the average vesicle size. A Transfersome® is a bi-component, most often vesicular, aggregate. The main functional characteristic of the aggregate is the extreme flexibility and permeability of its bilayer-like membrane coating. Its basis is the interdependency of local membrane shape and composition, which makes the bilayer self-regulating and self-optimising. The bilayer is thus capable of stress adaptation, via local and reversible bilayer component demixing.

Additional transdermal carriers include, but are not limited to, ethosomes, azone, castor oil derivatives, such as ethoxylated castor oil, jojoba oil derivatives, corn oil derivatives, emu oil derivatives, or any other suitable transdermal or transcutaneous carrier or carrier composition.

In an embodiment the transdermal carrier is propylene glycol, DMSO, or alcohol.

The transdermal carrier is typically used in an amount of about 1% (w/w) to about 35% (w/w). For example the amount of enhancer used may be about 1% (w/w), or about 2% (w/w), or about 3% (w/w), or about 4% (w/w), or about 5% (w/w), or about 6% (w/w), or about 7% (w/w), or about 8% (w/w), or about 9% (w/w), or about 10% (w/w), or about 11% (w/w), or about 12% (w/w), or about 13% (w/w), or about 14% (w/w), or about 15% (w/w), or about 16% (w/w), or about 17% (w/w), or about 18% (w/w), or about 19% (w/w), or about 20% (w/w), or about 21% (w/w), or about 22% (w/w), or about 23% (w/w), or about 24% (w/w), or about 25% (w/w), or about 26% (w/w), or about 27% (w/w), or about 28% (w/w), or about 29% (w/w), or about 30% (w/w) or about 29% (w/w), or about 30% (w/w), or about 31% (w/w), or about 32% (w/w), or about 33% (w/w), or about 34% (w/w), or about 35% (w/w), or about 36% (w/w), or about 37% (w/w), or about 38% (w/w), or about 39% (w/w), or about 40% (w/w), or about 41% (w/w), or about 42% (w/w), or about 43% (w/w), or about 44% (w/w), or about 45% (w/w), or about 46% (w/w), or about 47% (w/w), or about 48% (w/w), or about 49% (w/w), or about 50% (w/w).

In certain embodiments a transdermal enhancer is incorporated into the topical formulation or dosage form. The term "transdermal enhancer" as used herein refers to substances used to increase permeability and/or accelerate the delivery of a component of lyophilised cord blood plasma through the skin. Enhancers include monohydric alcohols such as ethyl, isopropyl, butyl and benzyl alcohols; or dihydric alcohols such as ethylene glycol, diethylene glycol, or propylene glycol dipropylene glycol and trimethylene glycol; or polyhydric alcohols such as glycerin, sorbitol and polyethylene glycol, which enhance drug solubility; polyethylene glycol ethers of aliphatic alcohols (such as cetyl, lauryl, oleyl and stearyl) including polyoxyethylene-4-lauryl ether, polyoxyethylene-2-oleyl ether and polyoxyethylene-10-oleyl ether; vegetable, animal and fish fats and oils such as cotton seed, corn, safflower, olive and castor oils, squalene, and lanolin; fatty acid esters such as propyl oleate, decyl oleate, isopropyl palmitate, glycol palmitate, glycol laurate, dodecyl myristate, isopropyl myristate and glycol stearate which enhance drug diffusibility; fatty acid alcohols such as oleyl alcohol and its derivatives; fatty acid amides such as oleamide and its derivatives; urea and urea derivatives such as allantoin which affect the ability of keratin to retain moisture; polar solvents such as dimethyldecylphosphoxide, methyloctylsulfoxide, dimethyllaurylamide, dodecylpyrrolidone, isosorbitol, dimethylacetonide, dimethylsulfoxide, decylmethylsulfoxide and dimethylformamide; salicylic acid; benzyl nicotinate; or higher molecular weight aliphatic surfactants such as lauryl sulfate salts, esters of sorbitol and sorbitol anhydride such as polysorbate. Other suitable enhancers include oleic and linoleic acids, triacetin, ascorbic acid, panthenol, butylated hydroxytoluene, tocopherol, tocopherol acetate, tocopheryl linoleate.

Other suitable transdermal enhancers include alcohols, amino acids, Azone® Azone-like compounds, so called soft penetration enhancers, sulphoxides, essential oils, fatty acids and fatty acid esters, macrophilic compounds, phospholipids and phospholipid derivatives and 2-pyrolidone derivatives.

In some embodiments enhancers are incorporated into the formulation in an amount typically up to about 30%. For example the amount of enhancer used may be about 0.05% (w/w), or about 0.1% (w/w), or about 0.5% (w/w), or about 1% (w/w), or about 2% (w/w), or about 3% (w/w), or about 4% (w/w), or about 5% (w/w), or about 6% (w/w), or about 7% (w/w), or about 8% (w/w), or about 9% (w/w), or about 10% (w/w), or about 11% (w/w), or about 12% (w/w), or about 13% (w/w), or about 14% (w/w), or about 15% (w/w), or about 16% (w/w), or about 17% (w/w), or about 18% (w/w), or about 19% (w/w), or about 20% (w/w), or about 21% (w/w), or about 22% (w/w), or about 23% (w/w), or about 24% (w/w), or about 25% (w/w), or about 26% (w/w), or about 27% (w/w), or about 28% (w/w), or about 29% (w/w), or about 30% (w/w).

Preparation of the Topical Formulation

In general the topical formulations are prepared by adding each of the components to the liposomal base and mixing to homogeneity. For example the lyophilised plasma or other blood product and transdermal enhancer, and any other optional components such as transdermal enhancers, exogenous cellular extracts, growth factors, hormones, metabolites, or peptides.

In some embodiments the lyophilised plasma or other blood product may be concentrated for example by evaporation, ultrafiltration, cross flow filtration or the like before addition to the liposomal base. In other embodiments the blood product may be fractionated for example by chromatography or precipitation of desired components using for example ammonium chloride to select for and/or concentrate desirable components. The concentration process results in an increased concentration of components such as cytokines, growth factors and chemokines in the blood product that forms part of the formulation. As a result of the concentration the blood products and hence the formulations, comprise supra-physiological levels of the components.

During preparation of the formulation at least a portion of the lyophilised plasma or other blood product and the transdermal carrier is incorporated into the liposomes of the liposomal base such that at least some of the liposomes contain at least a portion of the lyophilised plasma or other blood product and the transdermal carrier.

In embodiments where the formulations comprise a transdermal enhancer, a portion of the enhancer may also be present inside the liposome.

Methods

The formulations and dosage forms described herein can be used to treat, prevent or ameliorate at least one symptom or sign of a skin defect, for example by facilitation the transdermal delivery of a component of lyophilised plasma or other blood product. The methods typically comprise topical administration of the formulation to at least a portion of the skin of a subject having a skin defect in an amount sufficient to treat, prevent or ameliorate at least one symptom or sign the skin defect. In some embodiments the methods comprise administration of a component of a lyophilised plasma or other blood product using an oral dosage form selected from a sublingual troche, tablet, wafer or lozenge. In some embodiments the oral dosage form is a sublingual troche, buccal troche, tablet, wafer, lozenge or orally disintegrating tablet.

In other embodiments the formulation is administered to the nasal mucosa for example using a nasal applicator.

There is also provided a method of improving the quality of hair. In this embodiment the method includes the step of topically applying the formulation to an area of skin, for example, on the head, that has thinning hair or where hair is absent. It is believed that the lyophilised plasma or other blood products in the formulations and dosage forms contain components that assist in the reversal of hair follicle deterioration and are thereby useful in improving the quality of hair.

The formulations and dosage forms may also include extracts from natural mediums such as placenta extracts, extracts from Wharton's jelly, or amniotic fluids or components extracted from these tissues, or cord blood plasma, cord blood serum or components derived from them.

The formulation is preferably applied more than once. For example the formulation may be applied daily, twice daily, three times or more than three times daily. Application of the formula may be continued until the skin defect is resolved or prevented or until at least one symptom or sign of the skin defect is ameliorated. For example the formulation may be applied over a period of one week, two weeks, three weeks, four weeks, five weeks, six weeks, seven weeks, eight weeks, nine weeks, ten weeks, twelve weeks or longer.

The dosage from is preferably administered more than once. For example the dosage from maybe administered daily, twice daily, three times or more than three times daily. Administration of the dosage form may be continued until the skin defect is resolved or prevented or until at least one symptom or sign of the skin defect is ameliorated. For example the dosage form may be administered over a period of one week, two weeks, three weeks, four weeks, five weeks, six weeks, seven weeks, eight weeks, nine weeks, ten weeks, twelve weeks or longer.

In some embodiments application of the formulation or dosage from provides positive effects on skin defects and in some cases assists in the repair of the skin defects. Application of the formulation may have a soothing effect.

Application of the formulation or administration of the dosage form may also prevent or reduce scar formation. For example the formulation or dosage form may interfere with scar forming proteolytic enzymes (such as tryptase and chymase) or stimulate the inhibition of leucocytic elastatse to block mast cell activity.

Formulations for reducing or preventing scar formation may additionally contain hyaluronic acid (HA) or a salt thereof.

Application of the formulation or administration of the dosage form can also enhance the functional capacity of skin, enhance secretion of growth factors in the skin, enhance circulation to enhance skin regeneration, viability and/or elasticity. The formulations may also improve moisture uptake and retention in the skin by protecting against hypertonic and hypotonic stress, desiccation and dehydration, providing a barrier to inhibit tissue and moisture loss, progressively hydrating the different layers of the skin and softening hard tissue.

Application of the formulation or administration of the dosage form may enhance repair and reconstruction of the extracellular matrix and normal skin architecture, mitogenic activity, procollagen production, collagen production.

It is known that Young's modulus of the skin increases linearly with age. Young's modulus (or the elastic modulus) is a measure of stiffness and defines the relationship between stress (force per unit area) and strain (proportional deformation) in a material. Specifically, Young's modulus is the ratio of stress (pressure) to strain (which is dimensionless). Accordingly, Young's modulus has units of pressure, i.e. pascals or $N/m^2$ or $kg \cdot m^{-1} \cdot s^{-2}$). A high Young's modulus indicates that the material is inelastic and a low Young's modulus indicates that the material is elastic. For example rubber has an approximate Young's modulus of 0.01-0.1 MPa and concrete has an approximate Young's modulus of 30 GPa. Human skin has a Young's modulus of between 0.42 MPa and 0.85 MPa.

Young's modulus of skin can be measured by any method known in the art including Optical Coherence Elastography (OCE), mechanical stretching and suction tests.

Application of the formulation or administration of the dosage form results in a reduction of Young's modulus. For example application of the formulation or administration of the dosage form can result in a reduction of the Young's modulus by up to about 50% compared to the skin before treatment. For example the reduction may be about 5%, about 10%, about 15%, about 20%, about 25%, about 30%, about 35%, about 40%, about 45% or about 50%.

Application of the formulation or administration of the dosage form also reduces the number of visible fine lines and wrinkles. For example the number of visible fine lines may be reduced at least 50% compared to the skin before treatment. The reduction may be about 5%, about 10%, about 15%, about 20%, about 25%, about 30%, about 35%, about 40%, about 45% or at least about 50%. Similarly the number of wrinkles may be reduced by at least 50% compared to the skin before treatment. The reduction may be about 5%, about 10%, about 15%, about 20%, about 25%, about 30%, about 35%, about 40%, about 45% or at least 50%.

Skin Defects

The formulation are useful to treat, prevent or ameliorate at least one symptom or sign of a skin defect.

The skin defect may be a scar, a cosmetic skin defect, a traumatic skin defect, a chronic defect, a scar resulting from non-surgical/accidental trauma, a scar resulting from surgical trauma, a scar resulting from a chronic disease state, a scar resulting from topical irritation, depleted collagen levels, depleted elastin levels, depleted adhesive plaques at the dermal/epidermal junction, damage caused by age-related skin deterioration, collagen mis-alignment, scarring, scar formation, stretch marks, keloids, diabetic neuropathies, hardened-cracked skin, hardened cracked heel tissue, fine lines, wrinkles, or skin sagging.

The skin defect may also be poor skin texture, wrinkles, UV induced skin damage, skin aging, dry skin, dermatitis, eczema, rash, pruritus, sun burn, burns, stretch marks, acne scars, surgical scars.

In other embodiments the skin defect may be hair follicle deterioration or alopecia, Kits In one embodiment, a kit is provided including a formulation as described herein; a container; a label; and instructions which provide methods of applying the formulation. The instructions may be a pamphlet, CD, or other computer readable medium. Further, the instructions may provide information about a website which may contain downloadable content.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

In order that the present invention may be more clearly understood, preferred embodiments will be described with reference to the following drawings and examples.

Example 1—Plasma Formulation

Exemplary Plasma Topical Formulation

| Human plasma or plasma lysate: | 10 ml |
| Propylene Glycol | 10 gm |
| Liposomal base PCCA Lipoderm ® q.s. | 80 gm |

Example 2—Serum Formulation

Exemplary Serum Topical Formulation

| Human serum | 10 ml |
| Propylene Glycol | 10 gm |
| Liposomal base PCCA Lipoderm ® q.s. | 80 gm |

Example 3—PRP Formulation

Exemplary Serum Topical Formulation

| Human PRP (platelet rich plasma) | 10 ml |
| Propylene Glycol | 10 gm |
| Liposomal base PCCA Lipoderm ® q.s. | 80 gm |

Example 4—ACS Formulation

Exemplary Serum Topical Formulation

| Human Autologous conditioned serum | 10 ml |
| Propylene Glycol | 10 gm |
| Liposomal base PCCA Lipoderm ® q.s. | 80 gm |

Example 5—Preparation of Lyophilised Cord Plasma

Blood from multiple human umbilical cords was typed and cross matched and compatible blood was pooled and plasma prepared by centrifugation.

| Step | Temperature (° C.) | Time (mins) | Vacuum (microbar) |
| --- | --- | --- | --- |
| Primary drying | | | |
| 1 | −45 | 480 | 150 |
| Secondary drying | | | |
| 1 | −35 | 100 | 100 |
| 2 | −30 | 570 | 100 |
| 3 | −25 | 390 | 100 |
| 4 | −10 | 300* | 100 |
| 5 | −10 | 240 | 100 |
| 6 | 0 | 100* | 100 |
| 7 | 0 | 630 | 100 |
| Post Heat | | | |
| 1 | 20 | 1200 | 70 |

*Ramp time to reach indicated temperature

The lyophilised plasma was stored at room temperature, in darkness.

Example 6—Lyophilised Plasma Formulation—Sublingual Troche

Exemplary Sublingual Troche

| Lyophilised umbilical cord plasma | 1.7 gm |
| Gum acacia | 0.35 gm |
| Polyethylene glycol | 30.57 gm |
| Stevia | 0.64 gm |

The gum acacia, polyethylene glycol, stevia are melted together and mixed before the lyophilised plasma is added and mixed. Peppermint oil is also added as a flavour. The mixture is then poured into molds and allowed to cool to room temperature.

Example 7—Lyophilised Plasma Formulation

Exemplary Lyophilised Plasma Topical Formulation

| | |
|---|---|
| Lyophilised umbilical cord plasma | 10 gm |
| Propylene Glycol | 10 gm |
| Liposomal base PCCA Lipoderm ® q.s. | 80 gm |

Example 8—Cytokine, Chemokine and Growth Factor Profile of Reconstituted Lyophilised Plasma A sample of umbilical cord plasma used for lyophilisation was stored at −86° C. Two weeks after lyophilisation the product was reconstituted with water for injection (sterile). Both the original sample and reconstituted lyophilised plasma were stored frozen at −86° C. Additional samples including individual and pooled cord blood plasma (not lyophilised) and normal adult human plasma were also stored at −86° C. before assay.

The samples were assayed for the following Cytokine, Chemokine and Growth Factor using Biorad Bio-Plex® Multiplex Immunoassays according to the manufacturer's instructions.

eotaxin, IP-10, MCP-1, MIP-1α, MIP-1β and RANTES
VEGF, G-CSF, bFGF, TGF-β1, and PDGF-BB
IL1-receptor agonist, IL-1β, IL-4, IL-6, IL-7, IL-8, IL-9, IL-10, IL12p70, IL-13, IL17A, GM-CSF, TNFα and IFN-γ.

Figure 6:
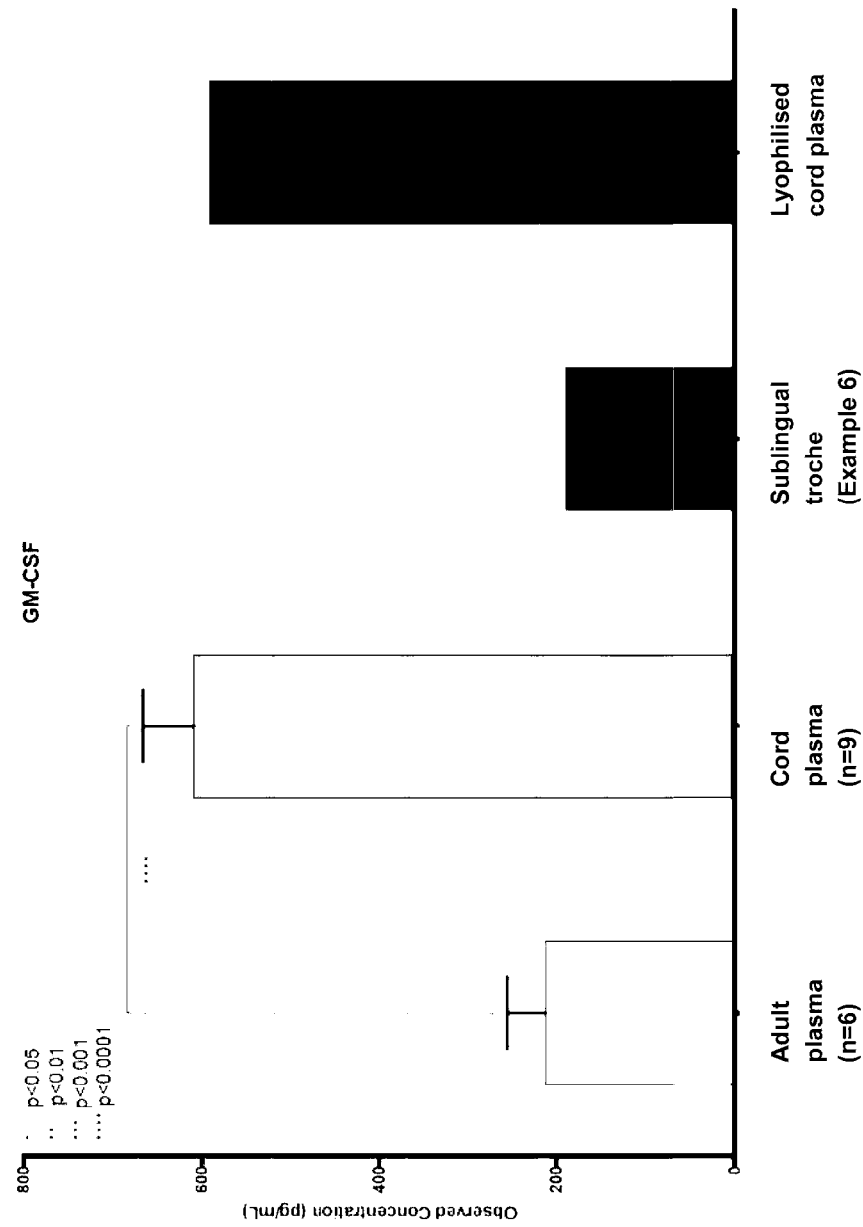
FIG. 6: Differences between healthy adult plasma, umbilical cord plasma, lyophilised reconstituted umbilical cord plasma, and the sublingual troche of Example 6 in relation to (A) GM-CSF; (B) IFN-γ; (C) TNFα; (D) IL-13; (E) MIP-1b(CCL4)
Figure 6:
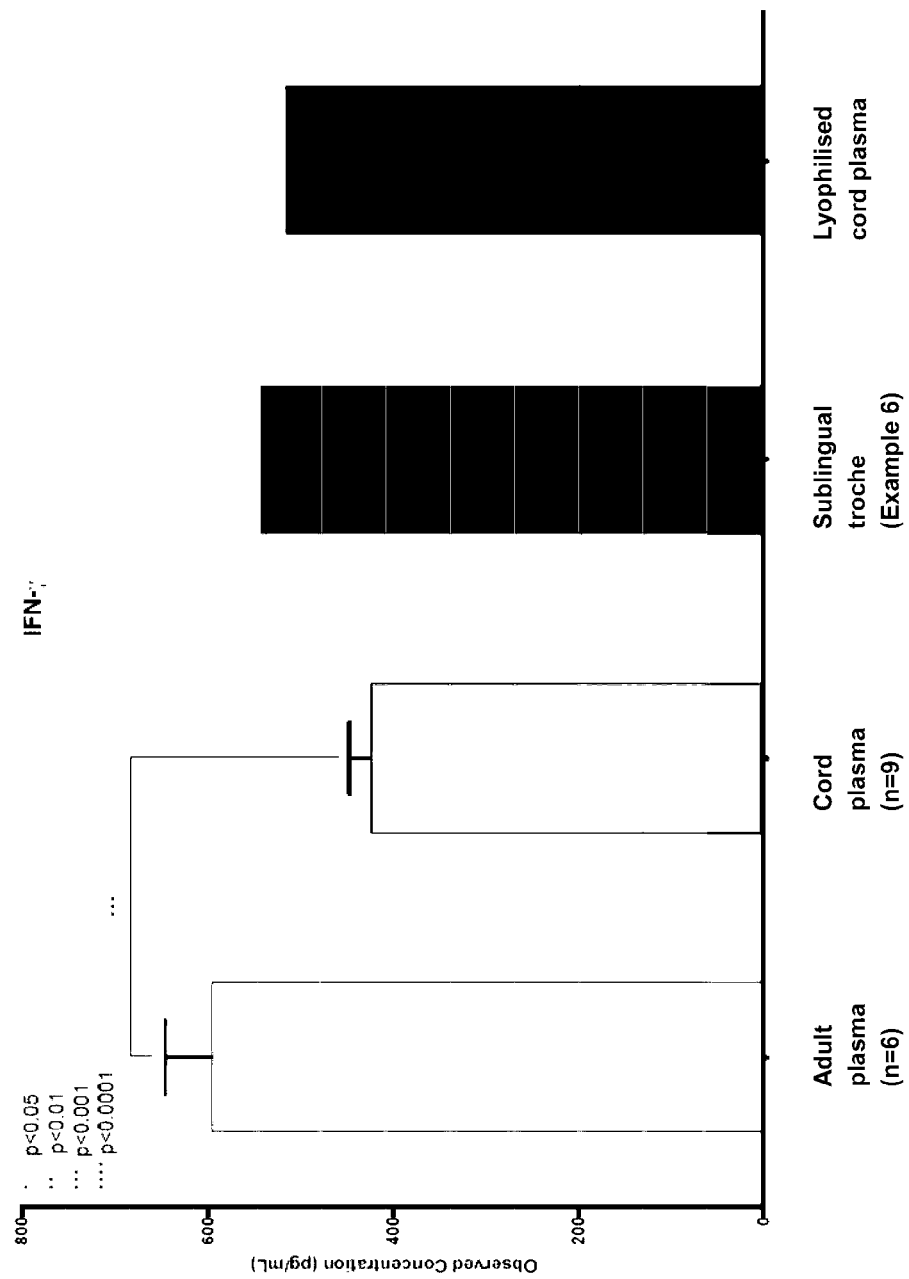
Figure 6:
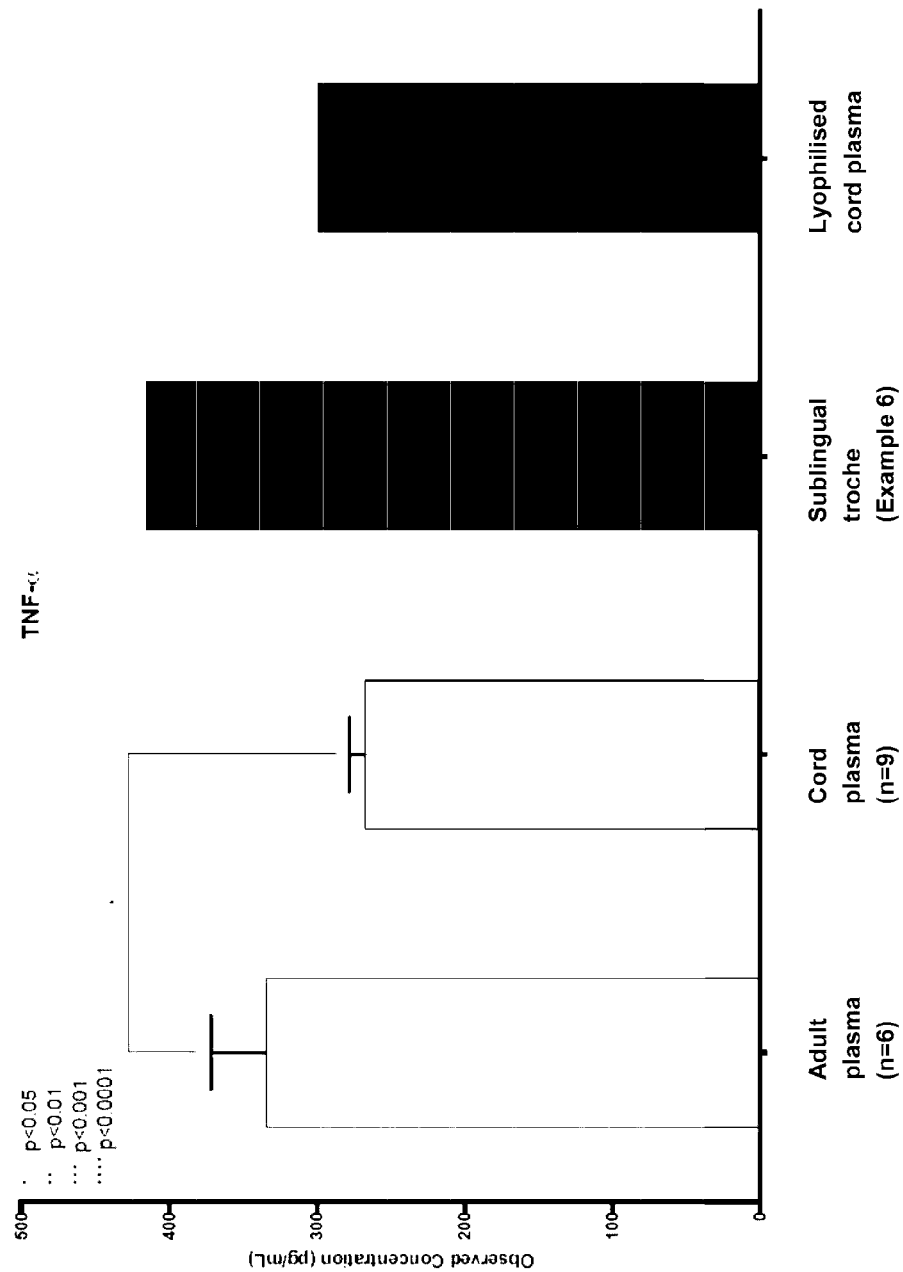
Figure 6:
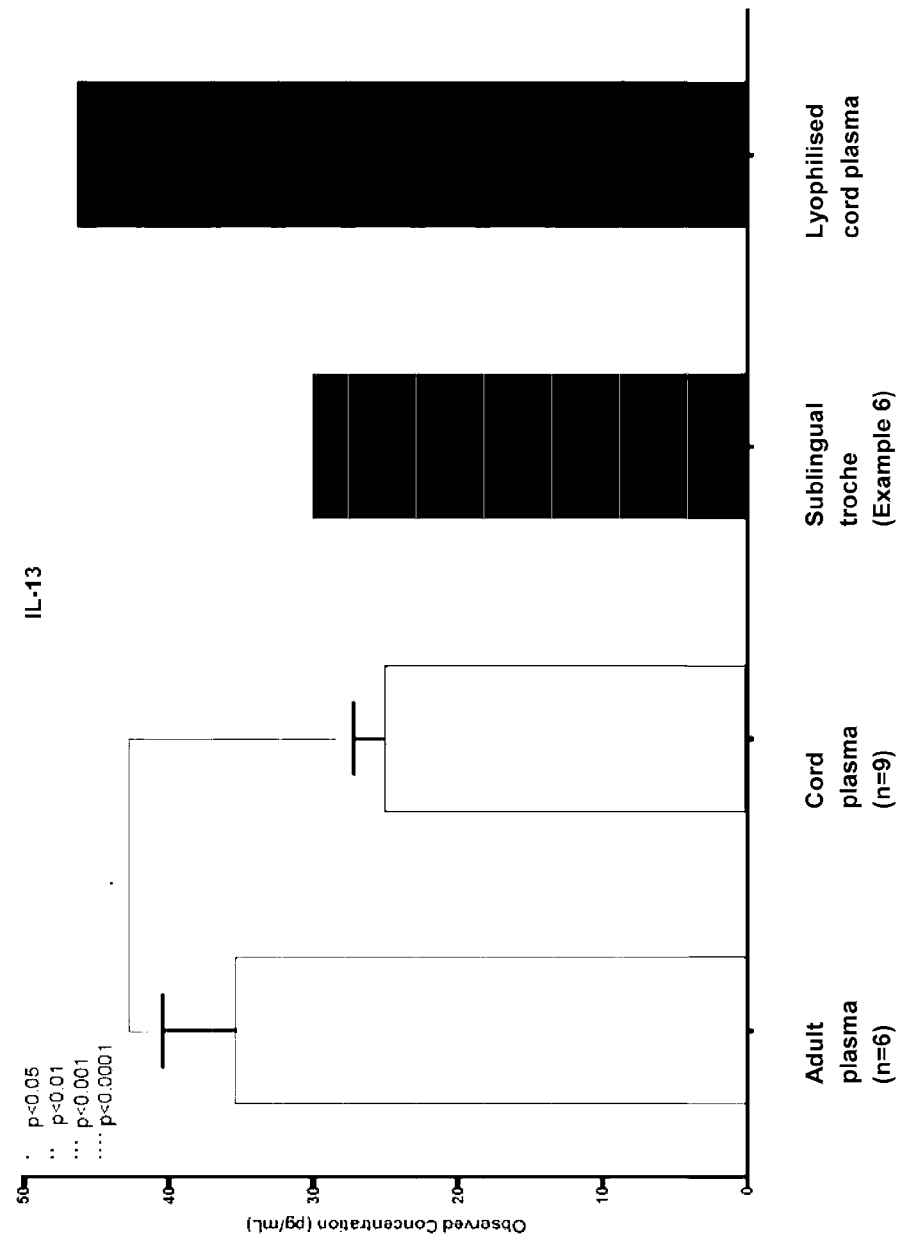
Figure 6:
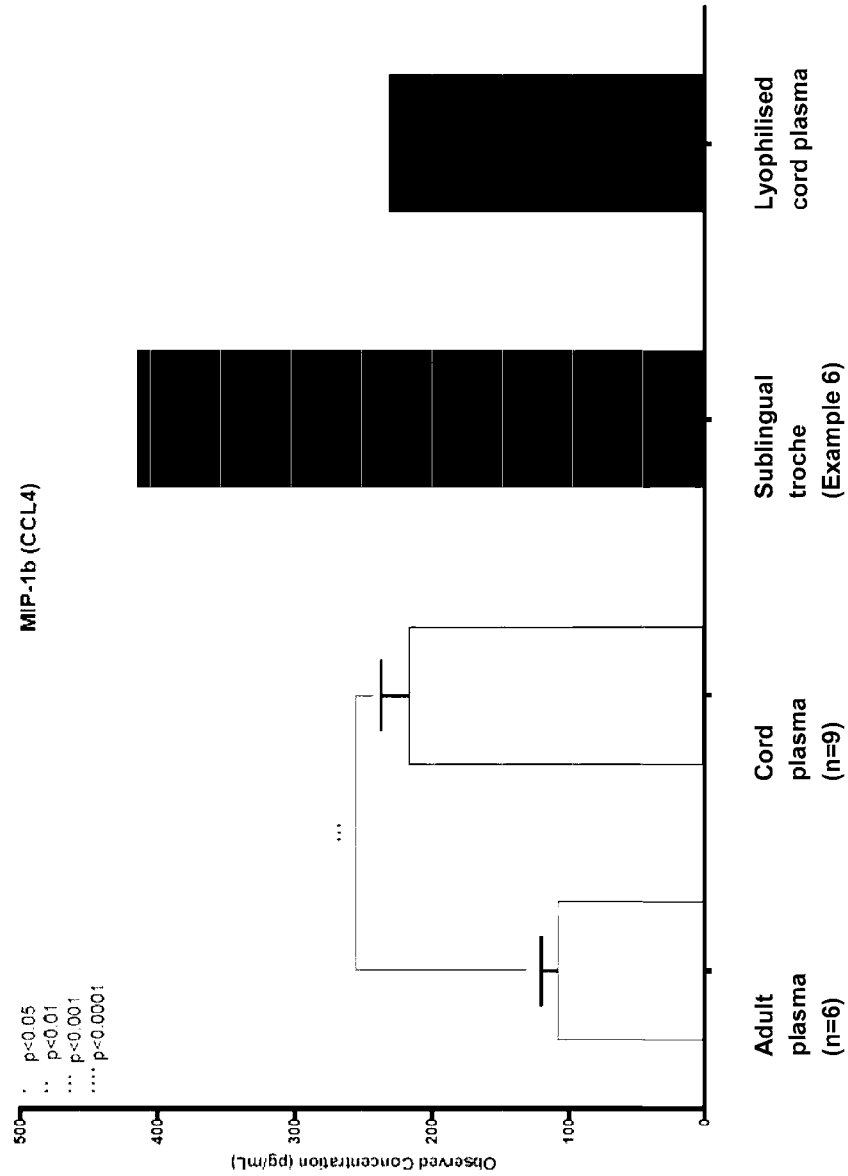

The assays provide a 'cytokine profile' for each sample which consists of the amount of each of the above components. Cytokine profiles for the samples are shown in FIGS. 1-5. FIG. 6 shows the relative amounts of individual components in different samples.

Example 9—Manufacturing Method

Each of the topical formulations is prepared using the following general procedure
Weigh Lipoderm (gel or cream) in a suitable container.
Transfer blood product (serum, plasma, PRP, ACS etc) under aseptic conditions to the Lidoderm.
Add additives such as hyaluronic acid, vitamins, antioxidants, transdermal carriers or enhancers.
Mix components with gentle agitation.
Seal the container and allow air to diffuse out of the gel.
Fill into appropriate tub or airless container.
Check pH.
Typically the formulation will have a pH from 6.0 to 7.0.

Example 10—Skin Rejuvenation

Subjects of good general health and with visible fine or deep wrinkles in the face, were chosen. Subjects with a history of, or active, skin disease were excluded. Subjects were asked to stop their current regime of skin care products. Make-up and sunscreens were permitted.
Treatment Regimen
The plasma formulation of Example 1 or Example 7 was applied in mornings and evenings to the facial skin for 6 weeks. A treatment group of 5 subjects were asked to document each application of the formulation. A second group was asked to apply a placebo comprising only the lipodermal base (PCCA Lipoderm®) according to the same treatment regimen.

Results
Subjects were evaluated by a visual assessment of skin quality prior to commencement of the treatment and again after the treatment was complete. Compared to the baseline observations all subjects in the treatment group had significant improvement in texture with the skin feeling firmer and more elastic. There was also a reduction in the number of visible fine lines and wrinkles. In comparison all subjects in the placebo group had no change in skin texture or in the number of visible fine lines and wrinkles compared to baseline observations.

The number of visible fine lines were reduced by 30% compared to the skin before treatment. Similarly the number of visible wrinkles were reduced by 30% compared to the skin before treatment.

All subjects liked the way the formulation felt and indicated that they would continue its regular use after the study period.

It will be appreciated by persons skilled in the art that numerous variations and/or modifications may be made to the technology as shown in the specific embodiments without departing from the spirit or scope of technology as broadly described. The present embodiments are, therefore, to be considered in all respects as illustrative and not restrictive.

The invention claimed is:
1. A formulation for skin rejuvenation comprising:
lyophilised umbilical cord plasma comprising at least one active chemokine, at least one growth factor and at least one cytokine;
a transdermal carrier; and
a liposomal base,
wherein at least a portion of the lyophilised umbilical cord plasma and transdermal
carrier are contained within liposomes of the liposomal base,
wherein the lyophilised umbilical cord plasma comprises:
eotaxin, IP-10, MCP-1, MIP-1α, MIP-1β and RANTES; and
VEGF, G-CSF, bFGF, TGF-β1, GDF-11 and PDGF-BB; and
IL1-receptor agonist, IL-1β, IL-4, IL-6, IL-7, IL-8, IL-9, IL-10, IL12p70, IL-13, IL17A, GM-CSF, TNFα and IFN-γ; and
the liposomal base is an emulsion of a mixture of about 60-80% wt/wt water, glycerin, $C_{12-15}$ alkyl benzoate, glyceryl stearate, dimethicone, cetearyl alcohol, cetearyl glucoside, polyacrylamide, cetyl alcohol, magnesium aluminum silicate, xanthan gum, Aloe vera, tocopheryl acetate, prunus amygadalus amara kernel oil, Vitis vinifera seed extract, Triticum vulgare germ oil, retinyl palmitate, ascorbyl palmitate, tetrasodium EDTA, phenoxyethanol, and sodium hydroxymethylglycinate.
2. The formulation of claim 1 wherein the lyophilised umbilical cord plasma is present in an amount selected from the group consisting of 1%, 2%, 3%, 4%, 5%, 6%, 7%, 8%, 9%, 10%, 11%, 12%, 13%, 14%, 15%, 16%, 17%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, and 80%.
3. The formulation of claim 1, wherein any one of the active chemokine, growth factor and cytokine is present in an amount selected from the group consisting of about

0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, and at least about 100 ng/g of dosage form.

4. The formulation of claim 1, wherein the transdermal carrier is selected from the group consisting of isopropyl alcohol, dipropylene glycol methyl-ether, butylated hydroxytoluene dipropylene glycol monomethyl-ether, 1-methoxy 2-propanol (glysolv PM/Icinol PM), ethylene glycol monobutylether (butyl glyxolv/butyl icinol), butyl di glysolv (butyl-icinol), Transcutol, propylene glycol (PG), N-methyl-2 pyrrolidone (NMP), methylene chloride, diethyl ether, ethanol, acetonitrile, ethyl acetate, benzyl alcohol, a combination of natural oil; ethylene glycol, propylene glycol, dimethyl polysiloxane (DMPX), oleic acid, caprylic acid, 1-octanol, ethanol (denatured or anhydrous), liposomal compositions, suitable plant oils, *Aloe vera* derivatives or sesame seed oil or derivatives thereof, acrylic polymers, rubber-based polymers, polysiloxane-based polymers, polyvinylpyrrolidone-based polymers, dimethylsulfoxide (DMSO), dimethylformamide (DMF), lecithin, vesicular aggregates, ethosomes, azone, castor oil derivatives, ethoxylated castor oil, jojoba oil derivatives, corn oil derivatives, propylene glycol, and emu oil derivatives.

5. The formulation of claim 1, wherein the transdermal carrier is present in an amount selected from the group consisting of 1% (w/w) 2% (w/w), 3% (w/w), 4% (w/w), 5% (w/w), or 6% (w/w), 7% (w/w), 8% (w/w), 9% (w/w), 10% (w/w), 11% (w/w), 12% (w/w), 13% (w/w), 14% (w/w), 15% (w/w), 16% (w/w), 17% (w/w), 18% (w/w), 19% (w/w), 20% (w/w), 21% (w/w), 22% (w/w), 23% (w/w), 24% (w/w), 25% (w/w), 26% (w/w), 27% (w/w), 28% (w/w), 29% (w/w), 30% (w/w), 29% (w/w), 30% (w/w), 31% (w/w), 32% (w/w), 33% (w/w), 34% (w/w), 35% (w/w), 36% (w/w), 37% (w/w), 38% (w/w), 39% (w/w), 40% (w/w), 41% (w/w), 42% (w/w), 43% (w/w), 44% (w/w), 45% (w/w), 46% (w/w), 47% (w/w), 48% (w/w), 49% (w/w), and 50% (w/w).

6. The formulation of claim 1, further comprising a transdermal enhancer.

7. The formulation of claim 6 wherein the transdermal enhancer is selected from the group consisting of ethyl alcohol, isopropyl alcohol, butyl alcohol, benzyl alcohol, ethylene glycol, diethylene glycol, propylene glycol, dipropylene glycol trimethylene glycol, glycerin, sorbitol, polyethylene glycol, polyoxyethylene-4-lauryl ether, polyoxyethylene-2-oleyl ether, polyoxyethylene-10-oleyl ether, cotton seed oil, corn oil, safflower oil, olive oil, castor oil, squalene, lanolin; propyl oleate, decyl oleate, isopropyl palmitate, glycol palmitate, glycol laurate, dodecyl myristate, isopropyl myristate, glycol stearate, oleyl alcohol, oleamide, dimethyldecylphosphoxide, methyloctylsulfoxide, dimethyllaurylamide, dodecylpyrrolidone, isosorbitol, dimethylacetonide, dimethylsulfoxide, decylmethylsulfoxide, dimethylformamide; salicylic acid; benzyl nicotinate; lauryl sulfate, sorbitol, polysorbate, linoleic acid, triacetin, ascorbic acid, panthenol, butylated hydroxytoluene, tocopherol, tocopherol acetate, and tocopheryl linoleate.

8. The formulation of claim 1, comprising:
1 to 80% (v/w) of the lyophilized plasma;
1% to 50% (w/w) of the transdermal carrier; and
up to 80% (w/w) of the liposomal base.

9. The formulation of claim 1, in a nasal dosage form or an oral dosage form selected from the group consisting of a sublingual troche, a tablet, a wafer, a lozenge, and a buccal troche.

10. A dosage form for skin rejuvenation comprising:
1 to 5% (w/w) lyophilised umbilical cord plasma comprising at least one active chemokine, at least one growth factor and at least one cytokine;
85 to 95% (w/w) polyethylene glycol; and
0.1 to 2% (w/w) gum acacia
wherein the lyophilised umbilical cord plasma comprises:
eotaxin, IP-10, MCP-1, MIP-1α, MIP-1β and RANTES; and
VEGF, G-CSF, bFGF, TGF-β1, GDF-11 and PDGF-BB; and
IL1-receptor agonist, IL-1β, IL-4, IL-6, IL-7, IL-8, IL-9, IL-10, IL12p70, IL-13, IL17A, GM-CSF, TNFα and IFN-γ; and
the liposomal base is an emulsion of a mixture of about 60-80% wt/wt water, glycerin, $C_{12-15}$ alkyl benzoate, glyceryl stearate, dimethicone, cetearyl alcohol, cetearyl glucoside, polyacrylamide, cetyl alcohol, magnesium aluminum silicate, xanthan gum, *Aloe vera*, tocopheryl acetate, prunus amygadalus amara kernel oil, *Vitis vinifera* seed extract, *Triticum vulgare* germ oil, retinyl palmitate, ascorbyl palmitate, tetrasodium EDTA, phenoxyethanol, and sodium hydroxymethylglycinate.

11. The dosage form of claim 10, further comprising a transdermal enhancer, enhancer or both a transdermal enhancer and an enhancer.

12. The dosage form of claim 10, wherein the lyophilised umbilical cord plasma is present in an amount selected from the group consisting of 1%, 2%, 3%, 4%, 5%, 6%, 7%, 8%, 9%, 10%, 11%, 12%, 13%, 14%, 15%, 16%, 17%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, and 80%.

13. The dosage form of claim 10, wherein any one of the active chemokine, growth factor or cytokine is present in an amount selected from the group consisting of about 0.1-1000 pg/g, about 1-1000 pg/g, about 50-1000 pg/g, about 100-1000 pg/g, about 200-1000 pg/g, about 300-1000 pg/g, about 400-1000 pg/g, about 500-1000 pg/g, about 600-1000 pg/g, about 700-1000 pg/g, about 800-1000 pg/g, about 900-1000 pg/g, about 1-100 ng/g, about 10-100 ng/g, about 10-100 ng/g, about 20-100 ng/g, about 30-100 ng/g, about 40-100 ng/g, about 50-100 ng/g, about 60-100 ng/g, about 170-100 ng/g, about 80-100 ng/g, about 90-100 ng/g, and at least about 100 ng/g of dosage form.

14. The dosage form of claim 10, containing an amount selected from the group consisting of about 0.1 mg, 0.5 mg, 1.0 mg, 5 mg, 10 mg, 15 mg, 25 mg, 35 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg 240 mg, 245 mg, and 250 mg of lyophilised plasma per dosage form.

15. The dosage form of claim 10, wherein the dosage form is an oral dosage form selected from the group consisting of a sublingual troche, a tablet, a wafer, a lozenge, a buccal troche.

16. A method of treating, preventing or ameliorating a symptom or sign of a skin defect, the method comprising administering to a subject in need thereof, a composition selected from the group consisting of the formulation of claim 1 and a dosage form comprising 1-5% (w/w) lyophilised umbilical cord plasma comprising at least one active chemokine, at least one growth factor and at least one cytokine; 85-95% (w/w) polyethylene glycol; and 0.1-2% (w/w) gum acacia.

17. The method of claim 16, wherein the dosage form or formulation is administered at least once per day.

18. The method of claim 16, wherein the skin defect is selected from the group consisting of poor skin texture, wrinkles, fine lines, UV induced skin damage, skin aging, dry skin, hair follicle deterioration, alopecia, dermatitis, eczema, rash, pruritus, sun burn, burns, stretch marks, acne scars, and surgical scars.

19. The method of claim 18 wherein the skin defect is wrinkles or fine lines and the treatment reduces the number of wrinkles or fine lines by an amount selected from the group consisting of up to 5%, up to 10%, up to 20%, up to 30%, up to 40% and at least 50%, compared to the number of wrinkles or fine lines before the treatment.

* * * * *